US011571391B2

(12) United States Patent
Deng et al.

(10) Patent No.: US 11,571,391 B2
(45) Date of Patent: Feb. 7, 2023

(54) ORAL DRUG DOSAGE FORMS COMPROMISING A FIXED-DOSE OF AN ADHD NON-STIMULANT AND AN ADHD STIMULANT

(71) Applicant: Triastek, Inc., Nanjing (CN)

(72) Inventors: Feihuang Deng, Nanjing (CN); Xiaoling Li, Dublin, CA (US); Senping Cheng, Nanjing (CN); Ying Wang, Nanjing (CN); Qing Luo, Nanjing (CN)

(73) Assignee: Triastek, Inc., Nanjing (CN)

( * ) Notice: Subject to any disclaimer, the term of this patent is extended or adjusted under 35 U.S.C. 154(b) by 132 days.

(21) Appl. No.: 16/960,867

(22) PCT Filed: Dec. 25, 2018

(86) PCT No.: PCT/CN2018/123400
§ 371 (c)(1),
(2) Date: Jul. 8, 2020

(87) PCT Pub. No.: WO2019/137200
PCT Pub. Date: Jul. 18, 2019

(65) Prior Publication Data
US 2021/0077410 A1    Mar. 18, 2021

(30) Foreign Application Priority Data
Jan. 9, 2018   (WO) ................ PCT/CN2018/071966

(51) Int. Cl.
*A61K 9/20*   (2006.01)
*B33Y 70/00*   (2020.01)
(Continued)

(52) U.S. Cl.
CPC .......... *A61K 9/2086* (2013.01); *A61K 9/2095* (2013.01); *A61K 31/137* (2013.01);
(Continued)

(58) Field of Classification Search
CPC .. A61K 9/2086; A61K 9/2095; A61K 31/137; A61K 31/155; A61K 31/4168;
(Continued)

(56) References Cited

U.S. PATENT DOCUMENTS

| 3,823,816 A | 7/1974 | Controulis et al. |
| 4,735,804 A | 4/1988 | Caldwell et al. |

(Continued)

FOREIGN PATENT DOCUMENTS

| CN | 103948557 A | 7/2004 |
| CN | 1216597 C | 8/2005 |

(Continued)

OTHER PUBLICATIONS

Anonymous (Aug. 1997). "Guidance For Industry: Dissolution Testing of Immediate Release Solid Oral Dosage Forms," Center for Drug Evaluation and Research, U.S. Food & Drug Administration. FDA-1997-D-0187, 17 pages.

(Continued)

*Primary Examiner* — Blessing M Fubara
(74) *Attorney, Agent, or Firm* — Morrison & Foerster LLP

(57) ABSTRACT

The present disclosure provides oral drug dosage forms comprising: (a) an erodible non-stimulant material admixed with an ADHD non-stimulant; and (b) an erodible stimulant material admixed with an ADHD stimulant, wherein the erodible non-stimulant material admixed with the ADHD non-stimulant is embedded in a substrate material, and wherein upon exposure to gastrointestinal fluid the ADHD non-stimulant is released according to a desired non-stimulant release profile and the ADHD stimulant is released according to a desired stimulant release profile. In some embodiment, the ADHD non-stimulant is released according to a sustained release profile. In some embodiments, the (Continued)

ADHD stimulant is released according to an immediate release profile. The oral drug dosage forms of the present disclosure are useful for the treatment of attention deficit hyperactivity disorder (ADHD). Also provided herein are methods of designing and manufacturing the oral drug dosage forms described herein.

21 Claims, 3 Drawing Sheets

(51) Int. Cl.
- B33Y 80/00 (2015.01)
- A61K 31/137 (2006.01)
- A61K 31/155 (2006.01)
- A61K 31/4168 (2006.01)
- A61K 31/4458 (2006.01)
- B33Y 10/00 (2015.01)

(52) U.S. Cl.
CPC ........ *A61K 31/155* (2013.01); *A61K 31/4168* (2013.01); *A61K 31/4458* (2013.01); *B33Y 70/00* (2014.12); *B33Y 80/00* (2014.12); *B33Y 10/00* (2014.12)

(58) Field of Classification Search
CPC .... A61K 31/4458; B33Y 70/00; B33Y 80/00; B33Y 10/00
See application file for complete search history.

(56) References Cited

U.S. PATENT DOCUMENTS

| | | |
|---|---|---|
| 5,198,229 A | 3/1993 | Wong |
| 5,204,055 A | 4/1993 | Sachs |
| 5,260,009 A | 11/1993 | Penn |
| 5,340,656 A | 8/1994 | Sachs |
| 5,342,624 A | 8/1994 | Mcneill |
| 5,387,380 A | 2/1995 | Cima |
| 5,490,962 A | 2/1996 | Cima |
| 5,503,785 A | 4/1996 | Crump |
| 5,518,690 A | 5/1996 | Masahashi |
| 5,543,155 A | 8/1996 | Fekete |
| 5,633,021 A | 5/1997 | Brown |
| 5,869,170 A | 2/1999 | Cima |
| 6,264,985 B1 | 7/2001 | Cremer |
| 6,280,771 B1 | 8/2001 | Monkhouse |
| 6,471,992 B1 | 10/2002 | Yoo |
| 6,514,518 B2 | 2/2003 | Monkhouse |
| 6,530,958 B1 | 3/2003 | Cima |
| 6,582,726 B1 | 6/2003 | Geysen |
| 6,685,962 B2 | 2/2004 | Friedman |
| 7,163,693 B1 | 1/2007 | Clarke |
| 7,276,252 B2 | 10/2007 | Payumo |
| 7,300,668 B2 | 11/2007 | Pryce Lewis |
| 7,314,640 B2 | 1/2008 | Sriwongjanya |
| 7,820,201 B2 | 10/2010 | Pryce Lewis |
| 7,875,290 B2 | 1/2011 | Payumo |
| 7,931,914 B2 | 4/2011 | Pryce Lewis |
| 8,088,415 B2 | 1/2012 | Wang |
| 8,465,777 B2 | 6/2013 | Wang |
| 8,673,352 B2 | 3/2014 | Sowden |
| 8,758,658 B2 | 6/2014 | Pryce Lewis |
| 8,828,411 B2 | 9/2014 | Yoo |
| 9,114,072 B2 | 8/2015 | Yoo |
| 9,314,429 B2 | 4/2016 | Jacob |
| 9,339,489 B2 | 5/2016 | Jacob |
| 10,143,626 B2 | 12/2018 | Li |
| 10,201,503 B1 | 2/2019 | Li |
| 10,258,575 B2 | 4/2019 | Li |
| 10,350,822 B1 | 7/2019 | Deng |
| 10,363,220 B2 | 7/2019 | Li |
| 10,624,857 B2 | 4/2020 | Li |
| 10,973,767 B2 | 4/2021 | Li |
| 11,278,499 B2 | 3/2022 | Li |
| 2001/0051185 A1* | 12/2001 | Faour .................. A61K 31/5375 424/468 |
| 2002/0015728 A1 | 2/2002 | Payumo |
| 2002/0106412 A1 | 8/2002 | Rowe |
| 2003/0143268 A1 | 7/2003 | Pryce Lewis |
| 2003/0147952 A1 | 8/2003 | Lim |
| 2003/0198677 A1 | 10/2003 | Pryce Lewis |
| 2004/0005360 A1 | 1/2004 | Wang |
| 2005/0249798 A1 | 11/2005 | Mohammad |
| 2006/0233881 A1 | 10/2006 | Sowden |
| 2008/0031119 A1 | 2/2008 | Ohnishi et al. |
| 2008/0220061 A1 | 9/2008 | Pryce Lewis |
| 2009/0148514 A1 | 6/2009 | Matthews |
| 2009/0317465 A1 | 12/2009 | Peppas |
| 2010/0226855 A1 | 9/2010 | Nangia |
| 2010/0233253 A1 | 9/2010 | Kavimandan et al. |
| 2011/0111022 A1 | 5/2011 | Kim et al. |
| 2011/0187015 A1 | 8/2011 | Pryce Lewis |
| 2011/0262496 A1* | 10/2011 | Desai .................. A61K 31/137 424/400 |
| 2012/0315333 A1 | 12/2012 | Zhou |
| 2013/0039960 A1* | 2/2013 | Desai ...................... A61K 9/50 514/654 |
| 2013/0337148 A1 | 12/2013 | Yang |
| 2013/0344149 A1 | 12/2013 | Stefan |
| 2015/0366801 A1 | 12/2015 | Jacob |
| 2016/0354315 A1 | 12/2016 | Li |
| 2017/0027872 A1 | 2/2017 | Wen |
| 2018/0116911 A1 | 5/2018 | Li |
| 2018/0214383 A1 | 8/2018 | Sun et al. |
| 2018/0311167 A1 | 11/2018 | Li |
| 2019/0192440 A1 | 6/2019 | Li |
| 2019/0209468 A1 | 7/2019 | Deng |
| 2019/0209482 A1 | 7/2019 | Li |
| 2019/0321299 A1 | 10/2019 | Li |
| 2020/0315971 A1 | 10/2020 | Li |
| 2020/0338009 A1 | 10/2020 | Li |
| 2021/0077410 A1 | 3/2021 | Deng et al. |
| 2021/0078244 A1 | 3/2021 | Deng et al. |
| 2021/0128479 A1 | 5/2021 | Cheng et al. |
| 2021/0154910 A1 | 5/2021 | Cheng et al. |
| 2021/0178677 A1 | 6/2021 | Liu et al. |
| 2021/0196638 A1 | 7/2021 | Deng et al. |
| 2021/0205226 A1 | 7/2021 | Li |

FOREIGN PATENT DOCUMENTS

| | | |
|---|---|---|
| CN | 101370483 A | 2/2009 |
| CN | 1620284 B | 4/2010 |
| CN | 105687153 A | 6/2016 |
| CN | 205343831 U | 6/2016 |
| CN | 106491551 A | 3/2017 |
| CN | 107019676 A | 8/2017 |
| CN | 108215153 A | 6/2018 |
| CN | 108215154 A | 6/2018 |
| CN | 207669820 U | 7/2018 |
| CN | 207901677 U | 9/2018 |
| CN | 105690762 A | 6/2019 |
| CN | 110787145 A | 2/2020 |
| CN | 111249257 A | 6/2020 |
| EP | 0631775 A1 | 1/1995 |
| EP | 1112739 A1 | 7/2001 |
| EP | 3302442 A1 | 4/2018 |
| EP | 3626439 A1 | 3/2020 |
| GB | 436236 A | 10/1935 |
| JP | 2020506918 A | 3/2020 |
| WO | 199009168 A1 | 8/1990 |
| WO | 199213521 A1 | 8/1992 |
| WO | 199836738 A1 | 8/1998 |
| WO | 199836739 A1 | 8/1998 |
| WO | 2000015199 A1 | 3/2000 |
| WO | 200137812 A2 | 5/2001 |
| WO | 200187272 A2 | 11/2001 |
| WO | 2003037244 A2 | 5/2003 |
| WO | 2003037607 A1 | 5/2003 |
| WO | 2003041690 A2 | 5/2003 |
| WO | 2003092633 A2 | 11/2003 |
| WO | 2004112755 A1 | 12/2004 |

(56) References Cited

FOREIGN PATENT DOCUMENTS

| WO | 2005027878 A1 | 3/2005 |
|---|---|---|
| WO | 2006058247 A2 | 6/2006 |
| WO | 2009050189 A2 | 4/2009 |
| WO | 2009084040 A1 | 7/2009 |
| WO | 2009144558 A1 | 12/2009 |
| WO | 2014143935 A1 | 9/2014 |
| WO | 2014144512 A1 | 9/2014 |
| WO | 2014144661 A1 | 9/2014 |
| WO | 2015095230 A1 | 6/2015 |
| WO | 2015187746 A1 | 12/2015 |
| WO | 2016075497 A1 | 5/2016 |
| WO | 2016192680 A1 | 12/2016 |
| WO | 2017152974 A1 | 9/2017 |
| WO | 2017153846 A2 | 9/2017 |
| WO | 2017193099 A1 | 11/2017 |
| WO | 2018137686 A1 | 8/2018 |
| WO | 2018210183 A1 | 11/2018 |
| WO | 2019025869 A1 | 2/2019 |
| WO | 2019137199 A1 | 7/2019 |
| WO | 2019137200 A1 | 7/2019 |
| WO | 2019137333 A1 | 7/2019 |
| WO | 2019224058 A1 | 11/2019 |
| WO | 2021031824 A1 | 2/2021 |
| WO | 2021042865 A1 | 3/2021 |
| WO | 2021164660 A1 | 8/2021 |
| WO | 2022089631 A1 | 5/2022 |
| WO | 2022121927 A1 | 6/2022 |

OTHER PUBLICATIONS

Brooke, D. et al. (Feb. 1977). "Zero-Order Drug Delivery System: Theory and Preliminary Testing," J. Pharm Sci. 66(2):159-162.

International Search Report, dated Aug. 29, 2016 for PCT Application No. PCT/CN2016/084838, filed Jun. 3, 2016, 4 pages.

Gibson, I. et al. (2015). "Additive Manufacturing Technologies: 3D Printing, Rapid Prototyping, and Direct Digital Manufacturing," 2nd ed. Johnson Matthey Technol. Rev. 59(3):193-198.

Goole, J. et al. (Feb. 2016, e-pub. Jan. 3, 2016). "3D printing In Pharmaceutics: A New Tool For Designing Customized Drug Delivery Systems," Int. J. Pharm. 499(1-2):376-394.

Goyanes, A. et al. (2015). "3D Printing: Engineering Novel Oral Devices With Unique Design and Drug Release Characteristics," Molecular Pharmaceutics 12(11):3783-4174, 24 pages.

International Preliminary Report on Patentability dated Jul. 30, 2019, for PCT Application No. PCT/CN2018/074146, filed Jan. 25, 2018, 5 pages.

International Preliminary Report On Patentability, dated Dec. 5, 2017 for PCT Application No. PCT/CN2016/084838, filed Jun. 3, 2016, 5 pages.

International Search Report and Written Opinion, dated Apr. 26, 2018, for PCT Application No. PCT/CN2018/074146, filed Jan. 25, 2018, 9 pages.

Katstra, W.E. et al. (Jun. 2001). "Fabrication Of Complex Oral Delivery Forms By Three Dimensional Printing™," Dissertation in Materials Science and Engineering, Massachusetts Institute of Technology.

Katstra, W.E. et al. (May 3, 2000). "Oral Dosage Forms Fabricated By Three Dimensional Printing," J. Control Release 66:1-9.

Khaled, S.A. et al. (2015). "3D Printing of Five-In-One Dose Combination Polypill With Defined Immediate and Sustained Release Profiles," School of Pharmacy, The University of Nottingham 217:308-314, 21 pages.

Khaled, S.A. et al. (Oct. 30, 2015, e-pub. Jul. 30, 2015). "3D Printing of Tablets Containing Multiple Drugs With Defined Release Profiles," Int. J. Pharm 494(2):643-650.

Lipper, R.A. et al. (Feb. 1977), "Analysis Of Theoretical Behavior Of A Proposed Zero-Order Drug Delivery System," J. Pharm Sci. 66(2):163-164.

Melchels, F.P.W. et al. (2010). "A Review On Stereolithography And its Application In Biomedical Engineering," Biomaterials 31:6121-6130, 22 pages.

Meyer, D.M. et al. (2010). "Anti-Inflammatory Activity and Neutrophil Reductions Mediated by the JAK1/JAK3 Inhibitor, CP-690,550, in Rat Adjuvant-Induced Arthritis," J. Inflammation 7:41, 12 pages.

Rawlings, J.S. et al. (2004). "The JAK/STAT Signaling Pathway," J. Cell Sci. 117(8):1281-1823.

Rowe C.W. et al. (May 3, 2000). "Multimechanism oral Dosage Forms Fabricated By Three Dimensional Printing™" Journal Of Controlled Release 66(1):11-17.

Schwartz, L. et al. (Jan. 1, 2017). "The Warburg Effect and the Hallmarks of Cancer," Nat Rev Drug Discov. 17(2):164-170, 26 pages.

Srikonda, S. et al. (2006). "Osmotic Controlled Drug Delivery Systems," Chapter 7 in Design Of Controlled Release Drug Delivery Systems, pp. 203-230.

Written Opinion Of The International Searching Authority, dated Aug. 29, 2016 for PCT Application No. PCT/CN2016/084838, filed Jun. 3, 2016, 4 pages.

Yoshida, T. et al. (Nov. 2013). "pH- and Ion-Sensitive Polymers For Drug Delivery," Expert Opinion Drug Delivery 10(11):1497-1513, 28 pages.

Abdul, S. et al. (2004). "A Flexible Technology for Modified Release of Drugs: Multi-Layered Tablets," Journal of Controlled Release 97:393-405.

Shende, P. et al. (2012). "Multi-Layer Tablet: Current Scenario and Recent Advances," International Journal of Drug Delivery 4:418-426.

Extended European Search Report, dated Mar. 11, 2022, for European Patent Application No. 21188195.8, 9 pages.

International Search Report and Written Opinion, dated Jan. 30, 2022, for PCT Application No. PCT/CN2020/127852, filed Nov. 1, 2021, 15 pages.

International Search Report and Written Opinion, dated Mar. 9, 2022, for PCT Application No. PCT/CN2020/136353, filed Dec. 8, 2021, 14 pages.

Thakral, S. et al. (2013). "Eudragit®: A Technology Evaluation," Expert Opin. Drug Deliv. 10(1):131-149.

\* cited by examiner

ORAL DRUG DOSAGE FORMS COMPROMISING A FIXED-DOSE OF AN ADHD NON-STIMULANT AND AN ADHD STIMULANT

CROSS REFERENCE TO RELATED APPLICATIONS

This application is a National Stage application under 35 U.S.C. § 371 of International Application No. PCT/CN2018/123400, filed on Dec. 25, 2018, which claims the priority benefit of PCT/CN2018/071966, filed on Jan. 9, 2018, the contents of each of which are incorporated herein by reference in their entirety and for all purposes.

TECHNICAL FIELD

The present disclosure provides stable oral drug dosage forms comprising: (a) an ADHD non-stimulant; and (b) an ADHD stimulant, wherein the oral drug dosage forms are configured and formulated to release the ADHD non-stimulant according to a desired non-stimulant release profile and release the ADHD stimulant according to a desired stimulant release profile. In some embodiments, the ADHD non-stimulant is released according to a sustained release profile. In some embodiments, the ADHD stimulant is released according to an immediate release profile. Also provided herein are methods of designing and manufacturing the oral drug dosage forms and methods for treating ADHD.

BACKGROUND

Attention deficit hyperactivity disorder (ADHD) is a common neurobiologic disorder characterized by age inappropriate levels of inattention, impulsivity, and hyperactivity. ADHD was long considered a childhood disorder, but there is growing awareness that ADHD is also a significant source of impairment for many teenagers and adults. The specific etiology of ADHD is unknown and there is no cure for ADHD. Standard treatments combining pharmacologic and behavioral therapies have demonstrated useful for controlling the symptoms of ADHD.

ADHD stimulants act via the neurotransmitter dopamine and are effective in reducing ADHD symptoms on a short-term basis. ADHD stimulants are used as first-line therapy for ADHD, however, 15% of patients do not respond optimally to monotherapy ADHD stimulant therapy. ADHD non-stimulants, and some antidepressants, are used as a second-line therapy for ADHD. ADHD non-stimulants act via different chemical receptors in the brain, and although they do not reduce ADHD symptoms quickly, the therapeutic effect can last up to 24 hours. Antidepressants, which require relatively larger doses, are prescribed less often due to associated side effects. Thus, there is still a need for improved ADHD treatments.

Oral medications are convenient for outpatient treatment of ADHD, however, issues regarding, for example, administration of multiple-active agent treatments, production of oral medications with fixed-doses of multiple active agents, production of multiple-active agent oral medications with individually controlled active agent pharmacokinetics, and patient compliance are well known in the art.

Some methods for production of multiple-active agent fixed-dose oral medications for controlled agent release are known in the art (see, e.g., WO2016192680, which is hereby incorporated by reference in its entirety).

BRIEF SUMMARY

In one aspect, the present disclosure provides oral drug dosage forms comprising: (a) an erodible non-stimulant material admixed with an ADHD non-stimulant; and (b) an erodible stimulant material admixed with an ADHD stimulant, wherein the erodible non-stimulant material admixed with the ADHD non-stimulant is embedded in a substrate material, and wherein upon exposure to gastrointestinal fluid the ADHD non-stimulant is released according to a sustained release profile. In some embodiments, the ADHD stimulant is released according to an immediate release profile. In some embodiments, the ADHD stimulant is released according to a sustained release profile. In some embodiments, the ADHD stimulant is released according to an immediate release profile and a sustained release profile.

In some embodiments, the oral drug dosage form comprises a multi-layered structure comprising a plurality of layers of the erodible non-stimulant material admixed with the ADHD non-stimulant. In some embodiments, the multi-layered structure comprises at least three layers of the erodible non-stimulant material admixed with the ADHD non-stimulant. In some embodiments, the multi-layered structure comprises four layers of the erodible non-stimulant material admixed with the ADHD non-stimulant. In some embodiments, each layer of the erodible non-stimulant material admixed with the ADHD non-stimulant of the multi-layered structure has a pre-determined surface area, thickness, and ADHD non-stimulant mass fraction correlating with the sustained release profile.

In some embodiments, the surface areas of two or more layers of the erodible non-stimulant material admixed with the ADHD non-stimulant of the multi-layered structure are different. In some embodiments, the surface area of each layer of the erodible non-stimulant material admixed with the ADHD non-stimulant of the multi-layered structure is between about 4.5 mm$^2$ to about 100 mm$^2$. In some embodiments, each successive layer of the erodible non-stimulant material admixed with the ADHD non-stimulant of the multi-layered structure, proceeding from the top layer to the bottom layer, has a smaller surface area. In some embodiments, each layer of the erodible non-stimulant material admixed with the ADHD non-stimulant of the multi-layered structure is concentrically positioned.

In some embodiments, the thicknesses of two or more layers of the erodible non-stimulant material admixed with the ADHD non-stimulant of the multi-layered structure are different. In some embodiments, the thickness of each layer of the erodible non-stimulant material admixed with the ADHD non-stimulant of the multi-layered structure is between about 0.2 mm to about 0.7 mm.

In some embodiments, the ADHD non-stimulant mass fraction is about 0.0001 to about 0.5.

In some embodiments, the substrate material is an insulating material that is impermeable to gastrointestinal fluid, wherein the insulating material forms a barrier between the gastrointestinal fluid and a portion of the erodible non-stimulant material. In some embodiments, the thickness of the barrier is at least about 0.2 mm. In some embodiments, the thickness of the barrier is at least about 0.4 mm. In some embodiments, the thickness of the barrier is at least about 1 mm.

In some embodiments, the oral drug dosage form further comprises a layer of the substrate material that forms a substrate rim, wherein the substrate rim forms a space, and wherein the space is on top of the multi-layered structure. In some embodiments, the space is not filled with a material. In some embodiments, the space is filled with an erodible material. In some embodiments, the space is filled with the erodible stimulant material admixed with the ADHD stimulant.

In some embodiments, the multi-layered structure further comprises an erodible intermediate material not admixed with the ADHD non-stimulant, and wherein the erodible intermediate material forms an intermediate layer between two or more layers of the erodible non-stimulant material admixed with the ADHD non-stimulant of the multi-layered structure.

In some embodiments, upon exposure to gastrointestinal fluid, the erodible non-stimulant material admixed with the ADHD non-stimulant and the erodible stimulant material admixed with the ADHD stimulant are simultaneously exposed to gastrointestinal fluid. In some embodiments, the erodible non-stimulant material admixed with the ADHD non-stimulant is separated from the erodible stimulant material admixed with the ADHD stimulant by the substrate material.

In some embodiments, upon exposure to gastrointestinal fluid, the erodible non-stimulant material admixed with the ADHD non-stimulant and the erodible stimulant material admixed with the ADHD stimulant are sequentially exposed to gastrointestinal fluid. In some embodiments, the erodible stimulant material admixed with the ADHD stimulant surrounds at least a portion of the erodible non-stimulant material admixed with the ADHD non-stimulant.

In some embodiments, the erodible stimulant material admixed with the ADHD stimulant is embedded in the substrate material.

In some embodiments, the erodible stimulant material admixed with the ADHD stimulant is physically separated from the erodible non-stimulant material admixed with the ADHD non-stimulant.

In some embodiments, the oral drug dosage form is configured and formulated to provide an immediate release profile of an ADHD stimulant. In some embodiments, the immediate release profile is 70% of the total ADHD stimulant release within about 30 minutes. In some embodiments, the immediate release profile is 85% of the total ADHD stimulant release within about 15 minutes.

In some embodiments, the erodible stimulant material admixed with the ADHD stimulant is a single-layered structure. In some embodiments, the erodible stimulant material admixed with the ADHD stimulant has a surface area of at least about 10 mm$^2$. In some embodiments, the erodible stimulant material admixed with the ADHD stimulant has a thickness of at least about 0.2 mm.

In some embodiments, the oral drug dosage form is configured and formulated to provide a sustained release profile of an ADHD stimulant. In some embodiments, the oral drug dosage form comprises a multi-layered structure comprising a plurality of layers of the erodible stimulant material admixed with the ADHD stimulant. In some embodiments, the multi-layered structure comprises at least three layers of the erodible stimulant material admixed with the ADHD stimulant. In some embodiments, each layer of the erodible stimulant material admixed with the ADHD stimulant of the multi-layered structure has a pre-determined surface area, thickness, and ADHD stimulant mass fraction correlating with the sustained release profile.

In some embodiments, the oral drug dosage form comprises a multi-layered structure comprising a plurality of layers, wherein a first layer of the plurality of layers comprises an erodible non-stimulant material admixed with the ADHD non-stimulant, and wherein a second layer of the plurality of layers comprises an erodible stimulant material admixed with the ADHD stimulant.

In some embodiments, the sustained release profile comprises a zero-order release profile, a first-order release profile, a delayed release profile, a pulsed release profile, an iterative pulsed release profile, or a combination thereof. In some embodiments, the sustained release profile is controlled, sustained ADHD non-stimulant release over at least about 5 hours.

In some embodiments, the amount of the ADHD non-stimulant in the oral drug dosage form is a sub-therapeutic dose when the ADHD non-stimulant is administered without the ADHD stimulant.

In some embodiments, the ADHD non-stimulant is clonidine or a pharmaceutically acceptable salt thereof. In some embodiments, the amount of clonidine or the pharmaceutically acceptable salt thereof in the oral drug dosage form is between about 0.05 mg to about 0.3 mg.

In some embodiments, the ADHD non-stimulant is atomoxetine or a pharmaceutically acceptable salt thereof. In some embodiments, the amount of atomoxetine or the pharmaceutically acceptable salt thereof in the oral drug dosage form is between about 2.5 mg to about 100 mg.

In some embodiments, the ADHD non-stimulant is guanfacine or a pharmaceutically acceptable salt thereof. In some embodiments, the amount of guanfacine or the pharmaceutically acceptable salt thereof in the oral drug dosage form is between about 0.5 mg to about 4 mg.

In some embodiments, the amount of the ADHD stimulant in the oral drug dosage form is a sub-therapeutic dose when the ADHD stimulant is administered without the ADHD non-stimulant.

In some embodiments, the ADHD stimulant is a methylphenidate or the pharmaceutically acceptable salt thereof. In some embodiments, the amount of the methylphenidate or the pharmaceutically acceptable salt thereof in the oral drug dosage form is between about 1.75 mg to about 60 mg. In some embodiments, the methylphenidate is dextromethylphenidate or a pharmaceutically acceptable salt thereof. In some embodiments, the amount of dextromethylphenidate or the pharmaceutically acceptable salt thereof in the oral drug dosage form is between about 1.75 mg to about 20 mg.

In some embodiments, the ADHD stimulant is an amphetamine. In some embodiments, the amphetamine is dextroamphetamine or a pharmaceutically acceptable salt thereof. In some embodiments, the amount of dextroamphetamine or the pharmaceutically acceptable salt thereof in the oral drug dosage form is between about 2.5 mg to about 50 mg.

In another aspect, the present disclosure provides oral drug dosage forms comprising: (a) a multi-layered structure comprising a plurality of layers an erodible non-stimulant material admixed with an ADHD non-stimulant, wherein the erodible non-stimulant material comprises hydroxyl propyl cellulose admixed with triethyl citrate, and wherein the ADHD non-stimulant is clonidine; and (b) an erodible stimulant material admixed with an ADHD stimulant, wherein the erodible stimulant material is vinylpyrrolidone-vinyl acetate copolymer admixed with triethyl citrate, and wherein the ADHD stimulant is dextromethylphenidate, wherein the erodible non-stimulant material admixed with the ADHD non-stimulant is embedded in a substrate material, and wherein upon exposure to gastrointestinal fluid the ADHD non-stimulant is released according to a sustained release profile and the ADHD stimulant is released according to an immediate release profile.

In another aspect, the present disclosure provides batches of an oral drug dosage form described herein.

In another aspect, the present disclosure provides methods for three-dimensional printing of a drug dosage form formulated and configured to provide a sustained drug release profile of an ADHD non-stimulant and an immediate drug release profile of an ADHD stimulant, wherein the oral drug dosage form comprises a multi-layered structure comprising a plurality of layers of an erodible non-stimulant material admixed with the ADHD non-stimulant, and wherein the erodible non-stimulant material is embedded in a substrate material, the method comprising: (a) dispensing the erodible non-stimulant material admixed with the ADHD non-stimulant based on a pre-determined thickness, surface area, and ADHD non-stimulant mass fraction; (b) dispensing an erodible stimulant material admixed with a ADHD stimulant; and (c) dispensing the substrate material.

In some embodiments, the method further comprises determining the thickness, surface area, and drug mass fraction of each layer of the multi-layered structure based on the sustained drug release profile of the ADHD non-stimulant. In some embodiments, the oral drug dosage form further comprises a layer of the substrate material that forms a substrate rim, wherein the substrate rim forms a space, and wherein the space is on top of the erodible non-stimulant material admixed with the ADHD non-stimulant. In some embodiments, the sustained drug release profile of the ADHD non-stimulant is controlled, sustained ADHD non-stimulant release over at least about 5 hours. In some embodiments, the immediate drug release profile of the ADHD stimulant is total ADHD stimulant release within about 30 minutes. In some embodiments, the immediate drug release profile of the ADHD stimulant is total ADHD stimulant release within about 1 hour. In some embodiments, the ADHD non-stimulant is clonidine or a pharmaceutically acceptable salt thereof and the ADHD stimulant is dextromethylphenidate or a pharmaceutically acceptable salt thereof.

In another aspect, the present disclosure provides methods for treating ADHD in an individual in need thereof, the method comprising administering to the individual an oral drug dosage form described herein. In some embodiments, the oral drug dosage form is administered once daily.

In one aspect, the present disclosure provides oral drug dosage forms prepared by a three-dimensional printing method, the method comprising: (a) dispensing an erodible non-stimulant material admixed with the ADHD non-stimulant based on a pre-determined thickness, surface area, and ADHD non-stimulant mass fraction for each layer of a multi-layered structure comprising a plurality of layers of the erodible non-stimulant material admixed with the ADHD non-stimulant; (b) dispensing an erodible stimulant material admixed with a ADHD stimulant; and (c) dispensing the substrate material, wherein the oral drug dosage form comprises the multi-layered structure comprising a plurality of layers of the erodible non-stimulant material admixed with the ADHD non-stimulant, wherein the multi-layered structure is embedded in the substrate, and wherein upon exposure to gastrointestinal fluid the ADHD non-stimulant is released according to a sustained release profile and the ADHD stimulant is released according to an immediate release profile.

These and other aspects and advantages of the present disclosure will become apparent from the subsequent detailed description and the appended claims. It is to be understood that one, some, or all of the properties of the various embodiments described herein may be combined to form other embodiments of the present disclosure.

BRIEF DESCRIPTION OF THE DRAWINGS

FIG. 1A shows a cross-section view of the exemplary oral drug dosage form 100. FIG. 1B and FIG. 1C show external views of alternate exemplary oral drug dosage forms 101, 102 having the cross-section illustrated in FIG. 1A.

FIG. 2A shows an external view of the exemplary oral drug dosage form 200 with translucently illustrated components to illustrate internal components of the oral drug dosage form 200. FIG. 2B shows a cross-section view of the exemplary dosage form 200.

DETAILED DESCRIPTION

Figure 1A:
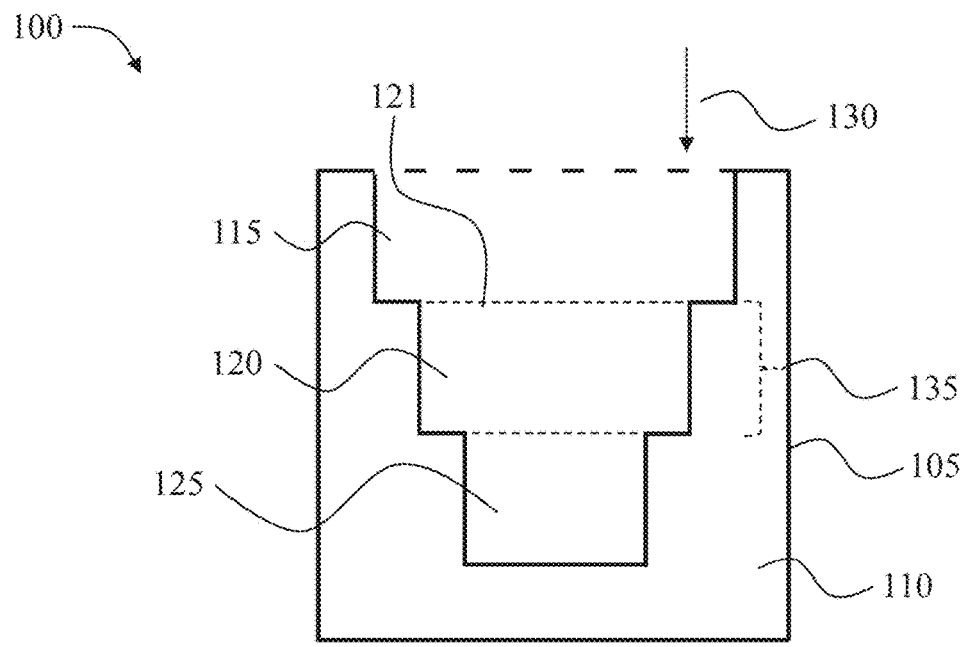
FIGS. 1A-1C show an exemplary oral drug dosage form 100 comprising a multi-layered structure comprising a plurality of layers 115, 120, 125 of an erodible non-stimulant material admixed with an ADHD non-stimulant.

The present disclosure describes oral drug dosage forms providing individually controlled release of a fixed-dose of an ADHD non-stimulant and a fixed-dose of an ADHD stimulant. The oral drug dosage forms described herein may be designed and produced to provide a desired drug release profile, or equivalent thereof, of the ADHD non-stimulant, e.g., a sustained release profile, and a desired drug release profile, or equivalent thereof, of the ADHD stimulant, e.g., an immediate release profile and/or a sustained release profile. The oral drug dosage forms of the present disclosure may be designed for production via a three-dimensional printing technique.

The oral drug dosage forms of the present disclosure provide, e.g., improved dosing accuracy, treatment efficacy, and patient compliance in comparison to traditional oral drug dosage forms currently available on the market for the treatment of ADHD. Furthermore, the oral drug dosage forms described herein may provide for a reduction of: the dose of individual active pharmaceutical ingredients in an oral drug dosage form, adverse events, and costs associated with treatment of ADHD.

Definitions

As used herein, "ADHD stimulant" refers to a central nervous system stimulant, or prodrug thereof, that elevates levels of norepinephrine in an individual. Exemplary ADHD stimulants include methylphenidate hydrochloride, dexmethylphenidate hydrochloride, methylphenidate (d,l), dexmethylphenidate, dextroamphetamine, dextroamphetamine sulfate, amphetamine sulfate, amphetamine aspartate, amphetamine sulfate, dextroamphetamine saccharate, lisdexamfetamine (prodrug), and lisdexamfetamine dimesylate.

As used herein, "ADHD non-stimulant" refers to an agent or prodrug thereof, other than an ADHD stimulant or ADHD stimulant prodrug, wherein the agent elevates levels of norepinephrine in an individual. Exemplary ADHD non-stimulant include atomoxetine, atomoxetine hydrochloride, guanfacine, guanfacine hydrochloride, clonidine, and clonidine hydrochloride.

As used herein, the term "pharmaceutically acceptable salt" refers to any pharmaceutically acceptable salt (e.g., acid or base) of a compound described herein, which, upon administration to an individual, is capable of providing the compound or an active metabolite or residue thereof to the individual. As is known to those of ordinary skill in the art, "salts" of the compounds described herein may be derived from inorganic or organic acids and bases. Examples of acids include, but are not limited to, hydrochloric, hydrobromic, sulfinuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds described herein and their pharmaceutically acceptable acid addition salts.

As used herein, "treat," "treatment," or "treating" is an approach for obtaining beneficial or desired results including clinical results. For purposes of this disclosure, beneficial or desired clinical results include, but are not limited to, one or more of the following: alleviating one or more symptoms resulting from the disease, decreasing the dose of one or more other medications required to treat the disease, and/or increasing the quality of life.

As used herein, the term "effective amount" refers to an amount of a compound or composition sufficient to treat a specified disorder, condition, or disease, such as ameliorate, palliate, lessen, and/or delay one or more of the symptoms of the disease.

As used herein, the term "individual" refers to a mammal and includes, but is not limited to, human, bovine, horse, feline, canine, rodent, or primate. In some embodiments, the individual is human.

The term "comprises" and grammatical equivalents thereof are used herein to mean that other components, ingredients, steps, etc. are optionally present. For example, an article "comprising" components A, B, and C may consist of (i.e., contain only) components A, B, and C, or may contain not only components A, B, and C but also one or more other components. It is understood that "comprises" and grammatical equivalents thereof include "consisting of" and "consisting essentially of."

Where a range of values is provided, it is understood that each intervening value, to the hundredth of the unit of the lower limit, unless the context clearly dictates otherwise, between the upper and lower limit of that range and any other stated or intervening value in that stated range, is encompassed within the disclosure (subject to any specifically excluded limit in the stated range). Where the stated range includes one or both of the limits, ranges excluding either or both of those included limits are also included in the disclosure.

Reference to "about" a value or parameter herein includes (and describes) variations that are directed to that value or parameter per se. For example, description referring to "about X" includes a description of "X."

As used herein, the singular forms "a," "or," and "the" include plural referents unless the context clearly dictates otherwise.

Oral Drug Dosage Forms

The present disclosure provides oral drug dosage form comprising: (a) an erodible non-stimulant material admixed with an ADHD non-stimulant; and (b) an erodible stimulant material admixed with an ADHD stimulant, wherein the erodible non-stimulant material admixed with the ADHD non-stimulant is embedded in a substrate material, and wherein upon exposure to gastrointestinal fluid the ADHD non-stimulant is released according to a sustained release profile and the ADHD stimulant is released according to a desired release profile. In some embodiments, the ADHD stimulant is released according to an immediate release profile. In some embodiments, the stimulant is released according to an immediate release profile and/or a sustained release profile.

In some embodiments, upon exposure to gastrointestinal fluid, the erodible non-stimulant material admixed with the ADHD non-stimulant and the erodible stimulant material admixed with the ADHD stimulant are simultaneously exposed to gastrointestinal fluid. In some embodiments, the erodible non-stimulant material admixed with the ADHD non-stimulant is separated from the erodible stimulant material admixed with the ADHD stimulant by a substrate material. In some embodiments, upon exposure to gastrointestinal fluid, the erodible non-stimulant material admixed with the ADHD non-stimulant and the erodible stimulant material admixed with the ADHD stimulant are sequentially exposed to gastrointestinal fluid. In some embodiments, upon exposure to gastrointestinal fluid, the erodible non-stimulant material admixed with the ADHD non-stimulant and the erodible stimulant material admixed with the ADHD stimulant are sequentially exposed to gastrointestinal fluid, wherein upon exposure to gastrointestinal fluid, the ADHD stimulant is released from the oral drug dosage form first. In some embodiments, the erodible non-stimulant material admixed with the ADHD non-stimulant and the erodible stimulant material admixed with the ADHD stimulant are configured as one or more layers of a multi-layered structure. In some embodiments, the erodible stimulant material admixed with the ADHD stimulant surrounds at least a portion of the erodible non-stimulant material admixed with the ADHD non-stimulant. In some embodiments, upon exposure to gastrointestinal fluid, the erodible non-stimulant material admixed with the ADHD non-stimulant and the erodible stimulant material admixed with the ADHD stimulant are sequentially exposed to gastrointestinal fluid, wherein upon exposure to gastrointestinal fluid, the ADHD non-stimulant is released from the oral drug dosage form first.

In some embodiments, the oral drug dosage form is an integrated dosage form (e.g., materials of the dosage form do not form components that may be readily separated).

The oral drug dosage forms described herein may be, for example, any size, shape, or weight that is suitable for oral administration. In some embodiments, the oral drug dosage form is suitable for oral administration to an individual, wherein the size, shape, and/or weight of the oral drug dosage form is based on an attribute of the individual. In some embodiments, the attribute of an individual is one or more of height, weight, or age. In some embodiments, the individual is an infant. In some embodiments, the individual is a child. In some embodiments, the individual is an adolescent. In some embodiments, the individual is an adult.

The oral drug dosage form described herein may be a personalized oral drug dosage form, wherein the personalized drug dosage form is tailored based on a patient's need(s). In some embodiments, the sustained release profile of an ADHD non-stimulant of an oral drug dosage form is adjusted, wherein the sustained release profile is based on a need of the patient. In some embodiments, the amount of an ADHD non-stimulant of an oral drug dosage form is adjusted, wherein the amount of the ADHD non-stimulant is based on a need of the patient. In some embodiments, the amount of an ADHD stimulant of an oral drug dosage form is adjusted, wherein the amount of the ADHD stimulant is based on a need of the patient. In some embodiments, the amount of an ADHD non-stimulant and the amount of an ADHD stimulant of an oral drug dosage form are adjusted, wherein the amount of the ADHD non-stimulant and the amount of ADHD stimulant is based on a need of the patient. In some embodiments, the amount of an ADHD stimulant and/or an ADHD non-stimulant is determined by titrating the amount of the ADHD stimulant and/or the ADHD non-stimulant.

In some embodiments, the largest dimension crossing an oral drug dosage form, e.g., largest diameter, is about 1 mm to about 25 mm, such as any of about 2 mm to about 10 mm, about 5 mm to about 12 mm, about 8 mm to about 15 mm, about 5 mm to about 10 mm, or about 7 mm to about 9 mm. In some embodiments, the largest dimension crossing an oral drug dosage form, e.g., largest diameter, is less than about 25 mm, such as less than about any of 24 mm, 23 mm, 22 mm, 21 mm, 20 mm, 19 mm, 18 mm, 17 mm, 16 mm, 15 mm, 14 mm, 13 mm, 12 mm, 11 mm, 10 mm, 9 mm, 8 mm, 7 mm, 6 mm, 5 mm, 4 mm, 3 mm, 2 mm, or 1 mm. In some embodiments, the largest dimension crossing an oral drug dosage form, e.g., largest diameter, is greater than about 1 mm, such as greater than about any of 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, or 25 mm. In some embodiments, the largest dimension crossing an oral drug dosage form, e.g., largest diameter, is about any of 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, or 25 mm.

In some embodiments, the oral drug dosage form has a thickness of about 1 mm to about 25 mm, such as any of about 2 mm to about 10 mm, about 5 mm to about 12 mm, about 8 mm to about 15 mm, about 5 mm to about 10 mm, or about 7 mm to about 9 mm. In some embodiments, the oral drug dosage form has a thickness of less than about 25 mm, such as less than about any of 24 mm, 23 mm, 22 mm, 21 mm, 20 mm, 19 mm, 18 mm, 17 mm, 16 mm, 15 mm, 14 mm, 13 mm, 12 mm, 11 mm, 10 mm, 9 mm, 8 mm, 7 mm, 6 mm, 5 mm, 4 mm, 3 mm, 2 mm, or 1 mm. In some embodiments, the oral drug dosage form has a thickness of greater than about 1 mm, such as greater than about any of 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, or 25 mm. In some embodiments, the oral drug dosage form has a thickness of about any of 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, or 25 mm.

In some embodiments, the shape of an oral drug dosage form comprises a cylinder, oval, bullet shape, arrow head shape, triangle, arced triangle, square, arced square, rectangle, arced rectangle, diamond, pentagon, hexagon, octagon, half moon, almond, or a combination thereof.

In some embodiments, the shape of an oral drug dosage form comprises a cylinder, oval, bullet shape, arrow head shape, triangle, arced triangle, square, arced square, rectangle, arced rectangle, diamond, pentagon, hexagon, octagon, half moon, almond, or a combination thereof, wherein the largest dimension crossing the oral drug dosage form, e.g., largest diameter, is about any of 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, or 25 mm.

In some embodiments, the total weight of an oral drug dosage form is about 20 mg to about 1500 mg, such as about any of about 50 mg to about 150 mg, about 150 mg to about 250 mg, about 160 mg to about 170 mg, about 250 mg to about 350 mg, about 350 mg to about 450 mg, about 450 mg to about 550 mg, about 550 mg to about 650 mg, about 650 mg to about 750 mg, about 750 mg to about 850 mg, about 850 mg to about 950 mg, about 950 mg to about 1050 mg, about 1050 mg to about 1150 mg, about 1150 mg to about 1250 mg, about 1250 mg to about 1350 mg, or about 1350 mg to about 1450 mg. In some embodiments, the total weight of an oral drug dosage form is less than about 1500 mg, such as less than about any of 1450 mg, 1400 mg, 1350 mg, 1300 mg, 1250 mg, 1200 mg, 1150 mg, 1100 mg, 1050 mg, 1000 mg, 950 mg, 900 mg, 850 mg, 800 mg, 750 mg, 700 mg, 650 mg, 600 mg, 550 mg, 500 mg, 475 mg, 450 mg, 425 mg, 400 mg, 375 mg, 350 mg, 325 mg, 300 mg, 275 mg, 250 mg, 225 mg, 200 mg, 175 mg, 150 mg, 125 mg, 100 mg, 95 mg, 90 mg, 85 mg, 80 mg, 75 mg, 70 mg, 65 mg, 60 mg, 55 mg, 50 mg, 45 mg, 40 mg, 35 mg, 30 mg, or 25 mg. In some embodiments, the total weight of an oral drug dosage form is greater than about 20 mg, such as greater than about any of 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, or 1450 mg. In some embodiments, the total weight of an oral drug dosage form is about any of 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg, 160 mg, 165 mg, 170 mg, 175 mg, 200 mg, 225 mg, 250 mg, 275 mg, 300 mg, 325 mg, 350 mg, 375 mg, 400 mg, 425 mg, 450 mg, 475 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, or 1450 mg.

The oral drug dosage forms of the present disclosure can further be coated, such as embedded, encased, or attached thereto, to, for example, (a) modify the taste, odor, and/or color of the oral drug dosage form; (b) protect the components of the oral drug dosage form from light, moisture, and/or air; (c) control the release of the components of the oral drug dosage form; (d) improve and/or alter the external appearance of the oral drug dosage form; (e) adjust position of drug release; (f) adjust texture of the oral drug dosage form; and (g) provide abuse deterrent features to the oral drug dosage form. In some embodiments, at least a portion of an oral drug dosage form is coated, such as embedded, encased, or attached thereto. In some embodiments, the oral drug dosage form is coated, such as embedded, encased, or attached thereto, with a sugar coating, e.g., an erodible material comprising sugar. In some embodiments, the oral drug dosage form is coated, such as embedded, encased, or attached thereto, with a film. In some embodiments, the oral drug dosage form is coated, such as embedded, encased, or attached thereto, with an enteric coating. In some embodiments, the oral drug dosage form is coated, such as embedded, encased, or attached thereto, with a gelatin layer.

In some embodiments, the oral drug dosage form has a surface area of about 20 mm$^2$ to about 700 mm$^2$. In some embodiments, the oral drug dosage form has a surface area of at least about 20 mm$^2$, such as at least about any of 30 mm$^2$, 40 mm$^2$, 50 mm$^2$, 60 mm$^2$, 70 mm$^2$, 80 mm$^2$, 90 mm$^2$, 100 mm$^2$, 125 mm$^2$, 150 mm$^2$, 175 mm$^2$, 200 mm$^2$, 225 mm$^2$, 250 mm$^2$, 275 mm$^2$, 300 mm$^2$, 325 mm$^2$, 350 mm$^2$, 375 mm$^2$, 400 mm$^2$, 425 mm$^2$, 450 mm$^2$, 475 mm$^2$, 500 mm$^2$, 525 mm$^2$, 550 mm$^2$, 575 mm$^2$, 600 mm$^2$, 625 mm$^2$, 650 mm$^2$, 675 mm$^2$, or 700 mm$^2$. In some embodiments, the oral drug dosage form has a surface area of less than about 700 mm$^2$, such as less than about any of 675 mm$^2$, 650 mm$^2$, 625 mm², 600 mm², 575 mm², 550 mm², 525 mm², 500 mm², 475 mm², 450 mm², 425 mm², 400 mm², 375 mm², 350 mm², 325 mm², 300 mm², 275 mm², 250 mm², 225 mm², 200 mm², 175 mm², 150 mm², 125 mm², 100 mm², 90 mm², 80 mm², 70 mm², 60 mm², 50 mm², 40 mm², or 30 mm². In some embodiments, the oral drug dosage form has a surface area of about any of 700 mm², 675 mm², 650 mm², 625 mm², 600 mm², 575 mm², 550 mm², 525 mm², 500 mm², 475 mm², 450 mm², 425 mm², 400 mm², 375 mm², 350 mm², 325 mm², 300 mm², 275 mm², 250 mm², 225 mm², 200 mm², 175 mm², 150 mm², 125 mm², 100 mm², 90 mm², 80 mm², 70 mm², 60 mm², 50 mm², 40 mm², 30 mm², or 20 mm².

A. Erodible Non-Stimulant Materials Admixed with an ADHD Non-Stimulant

The oral drug dosage forms described herein comprise an erodible non-stimulant material admixed with an ADHD non-stimulant, wherein the ADHD non-stimulant is released from the oral drug dosage form according to a sustained release profile. Generally, the erosion of an erodible non-stimulant material admixed with an ADHD non-stimulant correlates with the release rate of the ADHD non-stimulant from an oral drug dosage form.

In some embodiments, the oral drug dosage form comprises a multi-layered structure comprising a plurality of layers of an erodible non-stimulant material admixed with an ADHD non-stimulant. In some embodiments, erosion of a multi-layered structure comprising a plurality of layers of an erodible non-stimulant material admixed with an ADHD non-stimulant correlates with the release of the ADHD non-stimulant from an oral drug dosage form, wherein the ADHD non-stimulant is released from the oral drug dosage form according to a sustained release profile. For example, a multi-layered structure is illustrated in the oral drug dosage form 100 of FIG. 1A. The exemplary multi-layered structure contains three layers 115, 120, 125 of an erodible non-stimulant material admixed with an ADHD non stimulant embedded in a substrate material 110 (FIG. 1A). The multi-layered structures described herein may comprise any number of layers. In some embodiments, the multi-layered structure comprises at least three layers of an erodible non-stimulant material admixed with an ADHD non-stimulant. In some embodiments, the multi-layered structure comprises 3, 4, 5, 6, 7, 8, 9, 10, 11, 12, 13, 14, 15, 16, 17, 18, 19, or 20 layers of an erodible non-stimulant material admixed with an ADHD non-stimulant.

In some embodiments, each layer of an erodible non-stimulant material admixed with an ADHD non-stimulant of a multi-layered structure has a pre-determined surface area, thickness, and ADHD non-stimulant mass fraction correlating with a sustained release profile of the ADHD non-stimulant material.

Figure 1B:
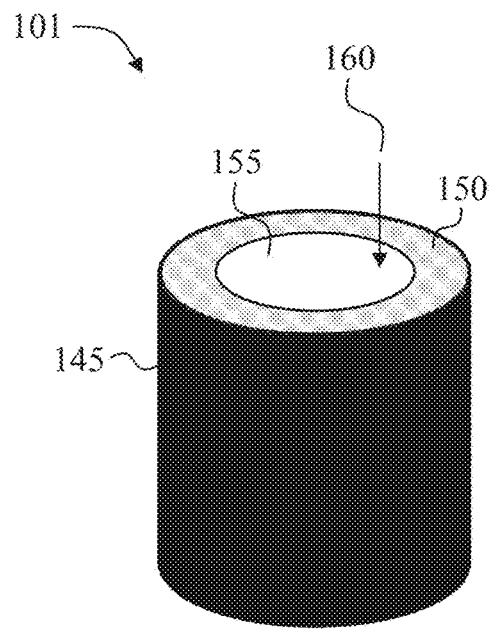
Figure 1C:
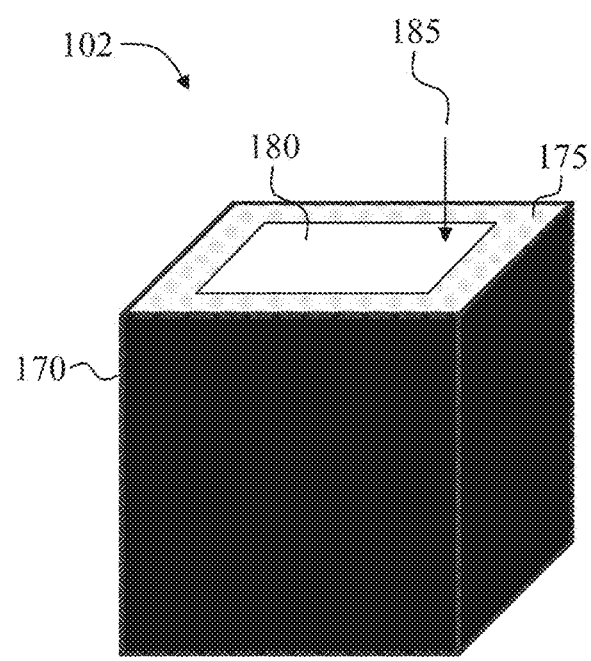

The surface area of a layer refers to the area of the surface of the layer exposed upon exposure to gastrointestinal fluid. For example, as illustrated in FIG. 1B, the top surface of the top layer (the layer first exposed to gastrointestinal fluid upon oral administration) of the multi-layered structure 155 of the oral drug dosage form 101 is exposed to gastrointestinal fluid following oral administration and represents the surface area of the top layer (e.g., the top layer 115 shown in the exemplary cross section view of FIG. 1A). In some embodiments, the surface areas of two or more layers of an erodible non-stimulant material admixed with an ADHD non-stimulant of a multi-layered structure are different. In some embodiments, the surface area of each layer of an erodible non-stimulant material admixed with an ADHD non-stimulant of a multi-layered structure is between about 1 mm² to about 100 mm², such as any of about 3 mm² to about 26 mm², or about 4.5 mm² to about 51 mm². In some embodiments, the surface area of each layer of an erodible non-stimulant material admixed with an ADHD non-stimulant of a multi-layered structure is at least about 10 mm², such as at least about any of 20 mm², 30 mm², 40 mm², 50 mm², 60 mm², or 70 mm².

In some embodiments, each successive layer of an erodible non-stimulant material admixed with the ADHD non-stimulant of a multi-layered structure, proceeding from the top to the bottom of the multi-layered structure, has a smaller surface area. The top of a multi-layered structure refers to a layer of an erodible non-stimulant material admixed with an ADHD non-stimulant of the multi-layered structure that is first contacted with gastrointestinal fluid upon oral administration. In preferred embodiments, the complete surface area of a successive layer of a multi-layered structure will be completely exposed to gastrointestinal fluid after a layer above has been fully eroded by gastrointestinal fluid. For example, as shown in FIG. 1A, when the top layer 115 of the multi-layered structure erodes, the complete surface area of the second layer 120 will be exposed to gastrointestinal fluid (the dashed line 121 indicates the cross-section view of the surface area of the second layer. In some embodiments, each layer of an erodible non-stimulant material admixed with an ADHD non-stimulant of a multi-layered structure is concentrically positioned.

The thickness of a layer is measured substantially in line with the direction of erosion of an erodible material from a surface that will first be exposed to a gastrointestinal fluid. For example, the thickness of a layer, e.g., 120, of a multi-layered structure is measured substantially in line with the direction of erosion 130 (the thickness of layer 120 is indicated by the dashed bracket 135) (FIG. 1A). In some embodiments, the thickness of a layer can be any thickness, such as a thickness suitable for production by 3D printing. In some embodiments, the thicknesses of two or more layers of an erodible non-stimulant material admixed with an ADHD non-stimulant of a multi-layered structure are different. In some embodiments, the thicknesses of two or more layers of an erodible non-stimulant material admixed with an ADHD non-stimulant of a multi-layered structure are the same.

In some embodiments, the thickness of each layer of an erodible non-stimulant material admixed with an ADHD non-stimulant of a multi-layered structure is between about 0.05 mm to about 1 mm, such as between about 0.1 mm to about 0.7 mm. In some embodiments, the thickness of a layer of an erodible non-stimulant material admixed with an ADHD non-stimulant of a multi-layered structure is less than about 1.0 mm, such as less than about any of 0.95 mm, 0.9 mm, 0.85 mm, 0.8 mm, 0.75 mm, 0.7 mm, 0.65 mm, 0.6 mm, 0.55 mm, 0.5 mm, 0.45 mm, 0.4 mm, 0.35 mm, 0.3 mm, 0.25 mm, 0.2 mm, 0.15 mm, 0.1 mm, or 0.05 mm. In some embodiments, the thickness of a layer of an erodible non-stimulant material admixed with an ADHD non-stimulant of a multi-layered structure is greater than about 0.01 mm, such as greater than about any of 0.05 mm, 0.1 mm, 0.15 mm, 0.2 mm, 0.25 mm, 0.3 mm, 0.35 mm, 0.4 mm, 0.45 mm, 0.5 mm, 0.55 mm, 0.6 mm, 0.65 mm, 0.7 mm, 0.75 mm, 0.8 mm, 0.85 mm, 0.9 mm, 0.95 mm, or 1 mm. In some embodiments, the thickness of a layer of an erodible non-stimulant material admixed with an ADHD non-stimulant of a multi-layered structure is about any of 0.65 mm, 0.52 mm, or 0.26 mm.

The drug mass fraction of a layer is the mass of the drug, e.g., an ADHD non-stimulant, in the layer of the erodible material admixed with the drug divided by the total mass of the layer of the erodible material admixed with the drug. In some embodiments, the drug mass faction of a layer of an erodible non-stimulant material admixed with an ADHD non-stimulant is at least about 0.0001, such as at least about any of 0.0005, 0.001, 0.005, 0.01, 0.02, 0.03, 0.04, 0.05, 0.06, 0.07, 0.08, 0.09, 0.1, 0.15, 0.2, 0.25, 0.3, 0.35, 0.4, 0.45, or 0.5. In some embodiments, the drug mass faction of a layer of an erodible non-stimulant material admixed with an ADHD non-stimulant is about any of 0.0001, 0.0005, 0.001, 0.005, 0.01, 0.02, 0.03, 0.04, 0.05, 0.06, 0.07, 0.08, 0.09, 0.1, 0.15, 0.2, 0.25, 0.3, 0.35, 0.4, 0.45, or 0.5. In some embodiments, the drug mass fractions of two or more layers of an erodible non-stimulant material admixed with an ADHD non-stimulant of a multi-layered structure are the same. In some embodiments, the drug mass fractions of two or more layers of an erodible non-stimulant material admixed with an ADHD non-stimulant of a multi-layered structure are different.

In some embodiments, the multi-layered structure comprises a top layer of a first erodible non-stimulant material admixed with an ADHD non-stimulant and another layer of a second erodible non-stimulant material admixed with the ADHD non-stimulant. In some embodiments, the multi-layered structure comprises a top layer of a first erodible non-stimulant material admixed with an ADHD non-stimulant and all other layers of a second erodible non-stimulant material admixed with the ADHD non-stimulant. In some embodiments, the first erodible non-stimulant material and the second erodible non-stimulant material are the same. In some embodiments, the first erodible non-stimulant material and the second erodible non-stimulant material are different. In some embodiments, the first erodible non-stimulant material and the second erodible non-stimulant material are different, wherein the erosion rate of the first erodible non-stimulant material is slower than the second erodible non-stimulant material.

i. Sustained Release Profiles

The oral drug dosage forms described herein provide release of an ADHD non-stimulant according to a sustained release profile. In some embodiments, the oral drug dosage forms described herein provide controlled (e.g., desired) release of an ADHD non-stimulant over at least about 4 hours, such as at least about any of 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, or 24 hours. In some embodiments, the oral drug dosage forms described herein provide controlled (e.g., desired) release of an ADHD non-stimulant over about any of 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, or 24 hours.

In some embodiments, the sustained release profile comprises a zero-order release profile, a first-order release profile, a delayed release profile, a pulsed release profile, an iterative pulsed release profile, or a combination thereof.

In some embodiments, the sustained release profile is similar, e.g., equivalent or bioequivalent, to a desired drug release profile or a release profile of a reference oral drug dosage form. The release profile, e.g., sustained release profile, of an oral drug dosage form may be evaluated using an in vitro dissolution rate of the oral drug dosage form. In some embodiments, the desired drug release profile, e.g., sustained release profile, of an oral drug dosage form is similar, e.g., equivalent or bioequivalent, to the in vitro dissolution rate of the oral drug dosage form. In some embodiments, the desired drug release profile of an oral drug dosage form is similar, e.g., equivalent or bioequivalent, to the in vivo drug release profile of the oral drug dosage form. In some embodiments, the in vivo drug release profile of an oral drug dosage form is based on evaluation of the in vitro dissolution rate of the oral drug dosage form. In some embodiments, the desired drug release profile of an oral drug dosage form is similar, e.g., equivalent or bioequivalent, to the release profile of a reference oral drug dosage form. Methods for in vitro dissolution testing and determining dissolution similarity are known in the art and the U.S. Food and Drug Administration has provided industry guidance on such methods (see Guidance for Industry; Dissolution Testing of Immediate Release Solid Oral Dosage Forms; CDER; August 1997).

Methods for in vitro dissolution testing include a logarithmic curve method, probability unit method, exponential model method, Weibull method, and Gompertz method. Statistical analysis methods for determining dissolution similarity of two dissolution profiles, e.g., an experimentally determined dissolution profile and a desired drug release profile, comprise regression analysis, ANOVA, similarity factor method, varying factor method, Splitpolt method, and Chow's method. In some embodiments, the dissolution similarity is evaluated using the similarity factor. In some embodiments, the dissolution similarity is evaluated using Chow's method.

In some embodiments, the release of the ADHD non-stimulant or ADHD stimulant is measured at one or more of about pH 2, about pH 7.0, and about pH 4.5.

In some embodiments, the oral drug dosage form releases an ADHD non-stimulant according to one or more of the following criteria: (i) about 20% to about 30% of the total ADHD non-stimulant is released at 1 hour after administration; (ii) about 35% to about 45% of the total ADHD non-stimulant is released at 2 hours after administration; (iii) about 60% to about 70% of the total ADHD non-stimulant is released at 4 hours after administration; (iv) about 75% to about 85% of the total ADHD non-stimulant is released at 6 hours after administration; (v) about 90% to about 100% of the total ADHD non-stimulant is released at 10 hours after administration; and (vi) about 95% to about 100% of the total ADHD non-stimulant is released at 12 hours after administration.

In some embodiments, the oral drug dosage form releases an ADHD non-stimulant according to one or more of the following criteria: (i) about 21% to about 29% of the total ADHD non-stimulant is released at 1 hour after administration; (ii) about 36% to about 44% of the total ADHD non-stimulant is released at 2 hours after administration; (iii) about 61% to about 69% of the total ADHD non-stimulant is released at 4 hours after administration; (iv) about 76% to about 84% of the total ADHD non-stimulant is released at 6 hours after administration; (v) about 91% to about 99% of the total ADHD non-stimulant is released at 10 hours after administration; and (vi) about 96% to about 100% of the total ADHD non-stimulant is released at 12 hours after administration.

In some embodiments, the oral drug dosage form releases an ADHD non-stimulant according to one or more of the following criteria: (i) about 22% to about 28% of the total ADHD non-stimulant is released at 1 hour after administration; (ii) about 37% to about 43% of the total ADHD non-stimulant is released at 2 hours after administration; (iii) about 62% to about 68% of the total ADHD non-stimulant is released at 4 hours after administration; (iv) about 77% to about 83% of the total ADHD non-stimulant is released at 6 hours after administration; (v) about 92% to about 98% of the total ADHD non-stimulant is released at 10 hours after administration; and (vi) about 97% to about 100% of the total ADHD non-stimulant is released at 12 hours after administration.

In some embodiments, the oral drug dosage form releases an ADHD non-stimulant according to one or more of the following criteria: (i) about 23% to about 27% of the total ADHD non-stimulant is released at 1 hour after administration; (ii) about 38% to about 42% of the total ADHD non-stimulant is released at 2 hours after administration; (iii) about 63% to about 67% of the total ADHD non-stimulant is released at 4 hours after administration; (iv) about 78% to about 82% of the total ADHD non-stimulant is released at 6 hours after administration; (v) about 93% to about 97% of the total ADHD non-stimulant is released at 10 hours after administration; and (vi) about 98% to about 100% of the total ADHD non-stimulant is released at 12 hours after administration.

In some embodiments, the oral drug dosage form releases an ADHD non-stimulant according to one or more of the following criteria: (i) about 24% to about 26% of the total ADHD non-stimulant is released at 1 hour after administration; (ii) about 39% to about 41% of the total ADHD non-stimulant is released at 2 hours after administration; (iii) about 64% to about 66% of the total ADHD non-stimulant is released at 4 hours after administration; (iv) about 79% to about 81% of the total ADHD non-stimulant is released at 6 hours after administration; (v) about 94% to about 96% of the total ADHD non-stimulant is released at 10 hours after administration; and (vi) about 99% to about 100% of the total ADHD non-stimulant is released at 12 hours after administration.

In some embodiments, the oral drug dosage form releases an ADHD non-stimulant according to one or more of the following criteria: (i) about 24% to about 28% of the total ADHD non-stimulant is released at 1 hour after administration; (ii) about 41% to about 45% of the total ADHD non-stimulant is released at 2 hours after administration; (iii) about 63% to about 67% of the total ADHD non-stimulant is released at 4 hours after administration; (iv) about 78% to about 82% of the total ADHD non-stimulant is released at 6 hours after administration; (v) about 95% to about 99% of the total ADHD non-stimulant is released at 10 hours after administration; and (vi) about 98% to about 100% of the total ADHD non-stimulant is released at 12 hours after administration.

In some embodiments, the oral drug dosage form releases an ADHD non-stimulant according to one or more of the following criteria: (i) about 22% to about 26% of the total ADHD non-stimulant is released at 1 hour after administration; (ii) about 38% to about 42% of the total ADHD non-stimulant is released at 2 hours after administration; (iii) about 61% to about 65% of the total ADHD non-stimulant is released at 4 hours after administration; (iv) about 75% to about 79% of the total ADHD non-stimulant is released at 6 hours after administration; (v) about 93% to about 97% of the total ADHD non-stimulant is released at 10 hours after administration; and (vi) about 98% to about 100% of the total ADHD non-stimulant is released at 12 hours after administration.

In some embodiments, the oral drug dosage form releases an ADHD non-stimulant according to one or more of the following criteria: (i) about 18% to about 22% of the total ADHD non-stimulant is released at 1 hour after administration; (ii) about 32% to about 36% of the total ADHD non-stimulant is released at 2 hours after administration; (iii) about 51% to about 55% of the total ADHD non-stimulant is released at 4 hours after administration; (iv) about 67% to about 71% of the total ADHD non-stimulant is released at 6 hours after administration; (v) about 89% to about 93% of the total ADHD non-stimulant is released at 10 hours after administration; and (vi) about 98% to about 100% of the total ADHD non-stimulant is released at 12 hours after administration.

ii. ADHD Non-Stimulants

The oral drug dosage forms described herein comprise an erodible non-stimulant material admixed with an ADHD non-stimulant. ADHD non-stimulants act by, e.g., (i) selectively inhibiting presynaptic norepinephrine transporters with secondary effects on dopaminergic systems (e.g., atomoxetine); (ii) selectively stimulating $\alpha_{2A}$-adrenergic receptors in the prefrontal cortex (e.g., guanfacine), and (iii) stimulating central $\alpha_{2A}$-adrenergic receptors to reduce sympathetic outflow (e.g., clonidine).

In some embodiments, the ADHD non-stimulant is a serotonin-norepinephrine reuptake inhibitor. In some embodiments, the ADHD non-stimulant is a dopamine transporter inhibitor. In some embodiments, the ADHD non-stimulant is a norepinephrine transporter inhibitor. In some embodiments, the ADHD non-stimulant is a serotonin transporter inhibitor. In some embodiments, the ADHD non-stimulant is an $\alpha_2$ adrenergic agonist. In some embodiments, the ADHD non-stimulant is an imidazoline receptor agonist.

In some embodiments, the ADHD non-stimulant is atomoxetine ((R)—N-methyl-3-phenyl-3-(o-tolyloxy)propan-1-amine), guanfacine, clonidine, or a pharmaceutically acceptable salt thereof, including atomoxetine HCl, guanfacine HCl, or clonidine HCl, or a combination thereof. In some embodiments, the ADHD non-stimulant is clonidine. In some embodiments, the ADHD non-stimulant is atomoxetine. In some embodiments, the ADHD non-stimulant is guanfacine.

In some embodiments, the oral drug dosage form comprises 2 or more ADHD non-stimulants. In some embodiments, the oral drug dosage form comprises clonidine and atomoxetine. In some embodiments, the oral drug dosage form comprises clonidine and guanfacine. In some embodiments, the oral drug dosage form comprises atomoxetine and guanfacine.

In some embodiments, the amount of an ADHD non-stimulant in an oral drug dosage form is a sub-therapeutic dose when the ADHD non-stimulant is not administered in conjunction with an ADHD stimulant.

In some embodiments, the amount of an ADHD non-stimulant in an oral drug dosage form is about 0.05 to about 110 mg, such as about 0.05 mg to about 0.25 mg, about 0.1 mg to about 0.2 mg, about 0.5 mg to about 5 mg, about 1 mg to about 4 mg, about 5 mg to about 110 mg, about 10 mg to about 100 mg, about 10 mg to about 25 mg, about 15 mg to about 60 mg, about 18 mg to about 80 mg, about 40 mg to about 80 mg, or about 40 mg to about 60 mg. In some embodiments, the amount of an ADHD non-stimulant in an oral drug dosage form is less than about 110 mg, such as less than about any of 100 mg, 95 mg, 90 mg, 85 mg, 80 mg, 75 mg, 70 mg, 65 mg, 60 mg, 55 mg, 50 mg, 45 mg, 40 mg, 35 mg, 30 mg, 25 mg, 20 mg, 18 mg, 15 mg, 10 mg, 9 mg, 8 mg, 7 mg, 6 mg, 5 mg, 4 mg, 3 mg, 2 mg, 1 mg, 0.5 mg, 0.4 mg, 0.3 mg, 0.2 mg, 0.1 mg, or 0.05 mg. In some embodiments, the amount of an ADHD non-stimulant in an oral drug dosage form is greater than about 0.05 mg, such as greater than about any of 0.1 mg, 0.2 mg, 0.3 mg, 0.4 mg, 0.5 mg, 1 mg, 2 mg, 3 mg, 4 mg, 5 mg, 6 mg, 7 mg, 8 mg, 9 mg, 10 mg, 15 mg, 18 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, or 110 mg. In some embodiments, the amount of an ADHD non-stimulant in an oral drug dosage form is about 0.05 mg, 0.1 mg, 0.2 mg, 0.3 mg, 0.4 mg, 0.5 mg, 1 mg, 2 mg, 3 mg, 4 mg, 5 mg, 6 mg, 7 mg, 8 mg, 9 mg, 10 mg, 15 mg, 18 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, or 110 mg.

In some embodiments, the ADHD non-stimulant of an oral drug dosage form is clonidine or a pharmaceutically acceptable salt thereof, wherein the amount of clonidine or the pharmaceutically acceptable salt thereof in the oral drug dosage form is between about 0.05 mg to about 0.3 mg. In some embodiments, the ADHD non-stimulant of an oral drug dosage form is clonidine or a pharmaceutically acceptable salt thereof, wherein the amount of clonidine or the pharmaceutically acceptable salt thereof in the oral drug dosage form is about any of 0.05 mg, 0.1 mg, 0.15 mg, 0.2 mg, 0.25 mg, or 0.3 mg.

In some embodiments, the ADHD non-stimulant of an oral drug dosage form is atomoxetine or a pharmaceutically acceptable salt thereof, wherein the amount of atomoxetine or the pharmaceutically acceptable salt thereof in the oral drug dosage form is between about 2.5 mg to about 100 mg. In some embodiments, the ADHD non-stimulant of an oral drug dosage form is atomoxetine or a pharmaceutically acceptable salt thereof, wherein the amount of atomoxetine or the pharmaceutically acceptable salt thereof in the oral drug dosage form is about any of 2.5 mg, 5 mg, 7.5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg or 100 mg.

In some embodiments, the ADHD non-stimulant of an oral drug dosage form is guanfacine or a pharmaceutically acceptable salt thereof, wherein the amount of guanfacine or the pharmaceutically acceptable salt thereof in the oral drug dosage form is between about 0.5 mg to about 4 mg. In some embodiments, the ADHD non-stimulant of the oral drug dosage form is guanfacine or a pharmaceutically acceptable salt thereof, wherein the amount of guanfacine or the pharmaceutically acceptable salt thereof in the oral drug dosage form is about any of 0.5 mg, 0.75 mg, 1 mg, 1.5 mg, 2 mg, 2.5 mg, 3 mg, 3.5 mg, or 4 mg.

Those of ordinary skill in the art will recognize that the provided list of ADHD non-stimulants and dosages is not limiting and recognize additional ADHD non-stimulant pharmaceuticals and dosages which will be useful with embodiments of the present disclosure.

B. Intermediate Layers

In some embodiments, the oral drug dosage forms comprising an ADHD non-stimulant described herein comprise a multi-layered structure further comprising an intermediate layer of an erodible intermediate material not admixed with the ADHD non-stimulant. In some embodiments, the intermediate layer is on top of the top layer of an erodible non-stimulant material admixed with an ADHD non-stimulant of a multi-layered structure.

In some embodiments, the oral drug dosage forms comprising an ADHD non-stimulant described herein comprise a multi-layered structure further comprising an erodible intermediate material not admixed with the ADHD non-stimulant, wherein the erodible intermediate material forms an intermediate layer between two or more layers of an erodible non-stimulant material admixed with the ADHD non-stimulant of the multi-layered structure. In some embodiments, the intermediate layer is between the top layer of an erodible non-stimulant material admixed with an ADHD on-stimulant material of a multi-layered structure and a subsequent layer of the erodible non-stimulant material admixed with the ADHD non-stimulant.

In some embodiments, the intermediate layer may modulate the release profile of a drug of an oral drug dosage form. In some embodiments, the oral drug dosage form comprising an intermediate layer has a delayed release profile or a pulsatile release profile.

C. Erodible Stimulant Materials Admixed with an ADHD Stimulant

The oral drug dosage forms described herein comprise an erodible stimulant material admixed with an ADHD stimulant, wherein the ADHD stimulant is released from the oral drug dosage form according to a desired stimulant release profile. Generally, the erosion of an erodible stimulant material admixed with an ADHD stimulant correlates with the release rate of the ADHD stimulant from an oral drug dosage form. The ADHD stimulant may be released according to any desired release profile, which may encompass the combination of two or more release profiles. In some embodiments, the ADHD stimulant is released from the oral drug dosage form according to an immediate release profile. In some embodiments, the ADHD stimulant is released from the oral drug dosage form according to a sustained release profile. In some embodiments, the ADHD stimulant is released from the oral drug dosage form according to an immediate release profile and a sustained release profile.

In some embodiments, the immediate release profile of an ADHD stimulant of an oral drug dosage form described herein is substantially similar to the release profile of the reference ADHD stimulant. In some embodiments, the immediate release profile of an ADHD stimulant of an oral drug dosage form described herein conforms with a release profile as measured via in vitro dissolution testing, e.g., releasing at least 85% or more of the total drug from the oral drug dosage form in 15 minutes in one or more or the following media: (1) 0.1 N HCl or Simulated Gastric Fluid USP without enzymes; (2) a pH 4.5 buffer; and (3) a pH 6.8 buffer or Simulated Intestinal Fluid USP without enzymes.

In some embodiments, the erodible stimulant material admixed with an ADHD stimulant is embedded in a substrate material.

In some embodiments, the erodible stimulant material admixed with an ADHD stimulant coats or contacts at least a portion of a substrate material or a multi-layered structure comprising a plurality of layers of an erodible non-stimulant material admixed with an ADHD non-stimulant.

In some embodiments, the erodible stimulant material admixed with an ADHD stimulant is a single-layered structure. In some embodiments, the erodible stimulant material admixed with an ADHD stimulant is a single-layered structure, wherein the single-layered structure has a pre-determined surface area, thickness, and ADHD stimulant mass fraction correlating with a desired release profile of the ADHD stimulant. In some embodiments, the erodible stimulant material admixed with an ADHD stimulant is a single-layered structure, wherein the single-layered structure has a pre-determined surface area, thickness, and ADHD stimulant mass fraction correlating with an immediate release profile of the ADHD stimulant. In some embodiments, the erodible stimulant material admixed with an ADHD stimulant is a single-layered structure, wherein the single-layered structure is embedded in a substrate material. In some embodiments, the erodible stimulant material admixed with an ADHD stimulant is a single-layered structure, wherein the single-layered structure is attached to a portion of an oral drug dosage form. In some embodiments, the oral drug dosage form comprises two or more single-layered structures comprising an erodible stimulant material admixed with an ADHD stimulant.

In some embodiments, the single-layered structure of an erodible stimulant material admixed with an ADHD stimulant has a surface area of at least about 10 mm$^2$, such as at least about any of 20 mm$^2$, 30 mm$^2$, 40 mm$^2$, 50 mm$^2$, 60 mm$^2$, 70 mm$^2$, 80 mm$^2$, 90 mm$^2$, or 100 mm$^2$.

In some embodiments, the single-layered structure of an erodible stimulant material admixed with an ADHD stimulant has a thickness of at least about 0.2 mm, such as at least about any of 0.25 mm, 0.5 mm, 0.75 mm, 1 mm, 1.5 mm, 2 mm, 2.5 mm, 3 mm, 3.5 mm, 4 mm, 4.5 mm, or 5 mm. In some embodiments, the erodible stimulant material admixed with an ADHD stimulant has a thickness of about 0.52 mm.

In some embodiments, the drug mass faction of a single-layered structure of an erodible stimulant material admixed with an ADHD stimulant is at least about 0.0001, such as at least about any of 0.0005, 0.001, 0.005, 0.01, 0.02, 0.03, 0.04, 0.05, 0.06, 0.07, 0.08, 0.09, 0.1, 0.15, 0.2, 0.25, 0.3, 0.35, 0.4, 0.45, or 0.5. In some embodiments, the drug mass faction of a single-layered structure of an erodible stimulant material admixed with an ADHD stimulant is about any of 0.0001, 0.0005, 0.001, 0.005, 0.01, 0.02, 0.03, 0.04, 0.05, 0.06, 0.07, 0.08, 0.09, 0.1, 0.15, 0.2, 0.25, 0.3, 0.35, 0.4, 0.45, or 0.5.

In some embodiments, the oral drug dosage form comprises a multi-layered structure comprising a plurality of layers of an erodible stimulant material admixed with an ADHD stimulant. In some embodiments, erosion of a multi-layered structure comprising a plurality of layers of an erodible stimulant material admixed with an ADHD stimulant correlates with the release of the ADHD stimulant from an oral drug dosage form. In some embodiments, the ADHD stimulant is released from the oral drug dosage form according to a sustained release profile. One of ordinary skill in the art will readily understand that the same concepts regarding multi-layered structure for configuring and formulating a desired drug release profile of an ADHD non-stimulant discussed above apply and teach configuring and formulating a desired drug release profile of an ADHD stimulant.

In some embodiments, the multi-layered structure comprising a plurality of layer of an erodible stimulant material admixed with an ADHD stimulant is embedded in a substrate material.

The multi-layered structures comprising an erodible stimulant material admixed with an ADHD stimulant described herein may comprise any number of layers. In some embodiments, the multi-layered structure comprises at least three layers of an erodible stimulant material admixed with an ADHD stimulant. In some embodiments, the multi-layered structure comprises 3, 4, 5, 6, 7, 8, 9, 10, 11, 12, 13, 14, 15, 16, 17, 18, 19, or 20 layers of an erodible stimulant material admixed with an ADHD stimulant.

In some embodiments, each layer of an erodible stimulant material admixed with an ADHD stimulant of a multi-layered structure has a pre-determined surface area, thickness, and ADHD stimulant mass fraction correlating with a sustained release profile of the ADHD stimulant.

In some embodiments, the surface areas of two or more layers of the erodible stimulant material admixed with the ADHD stimulant of the multi-layered structure are different. In some embodiments, each successive layer of the erodible stimulant material admixed with the ADHD stimulant of the multi-layered structure, proceeding from the top layer to the bottom layer, has a smaller surface area. In some embodiments, each layer of the erodible stimulant material admixed with the ADHD stimulant of the multi-layered structure is concentrically positioned.

In some embodiments, the surface area of each layer of an erodible stimulant material admixed with an ADHD stimulant of a multi-layered structure is between about 1 mm$^2$ to about 100 mm$^2$, such as any of about 3 mm$^2$ to about 26 mm$^2$, or about 4.5 mm$^2$ to about 51 mm$^2$. In some embodiments, the surface area of each layer of an erodible stimulant material admixed with an ADHD stimulant of a multi-layered structure is at least about 10 mm$^2$, such as at least about any of 20 mm$^2$, 30 mm$^2$, 40 mm$^2$, 50 mm$^2$, 60 mm$^2$, or 70 mm$^2$.

In some embodiments, the thickness of a layer can be any thickness, such as a thickness suitable for production by 3D printing. In some embodiments, the thicknesses of two or more layers of an erodible stimulant material admixed with an ADHD stimulant of a multi-layered structure are different. In some embodiments, the thicknesses of two or more layers of an erodible stimulant material admixed with an ADHD stimulant of a multi-layered structure are the same.

In some embodiments, the thickness of each layer of an erodible stimulant material admixed with an ADHD stimulant of a multi-layered structure is between about 0.05 mm to about 1 mm, such as between about 0.2 mm to about 0.7 mm. In some embodiments, the thickness of a layer of an erodible stimulant material admixed with an ADHD stimulant of a multi-layered structure is less than about 1.0 mm, such as less than about any of 0.95 mm, 0.9 mm, 0.85 mm, 0.8 mm, 0.75 mm, 0.7 mm, 0.65 mm, 0.6 mm, 0.55 mm, 0.5 mm, 0.45 mm, 0.4 mm, 0.35 mm, 0.3 mm, 0.25 mm, 0.2 mm, 0.15 mm, 0.1 mm, or 0.05 mm. In some embodiments, the thickness of a layer of an erodible stimulant material admixed with an ADHD stimulant of a multi-layered structure is greater than about 0.01 mm, such as greater than about any of 0.05 mm, 0.1 mm, 0.15 mm, 0.2 mm, 0.25 mm, 0.3 mm, 0.35 mm, 0.4 mm, 0.45 mm, 0.5 mm, 0.55 mm, 0.6 mm, 0.65 mm, 0.7 mm, 0.75 mm, 0.8 mm, 0.85 mm, 0.9 mm, 0.95 mm, or 1 mm. In some embodiments, the thickness of a layer of an erodible stimulant material admixed with an ADHD stimulant of a multi-layered structure is about any of 0.65 mm, 0.52 mm, or 0.26 mm.

In some embodiments, the drug mass faction of a layer of an erodible stimulant material admixed with an ADHD stimulant is at least about 0.0001, such as at least about any of 0.0005, 0.001, 0.005, 0.01, 0.02, 0.03, 0.04, 0.05, 0.06, 0.07, 0.08, 0.09, 0.1, 0.15, 0.2, 0.25, 0.3, 0.35, 0.4, 0.45, or 0.5. In some embodiments, the drug mass faction of a layer of an erodible stimulant material admixed with an ADHD stimulant is about any of 0.0001, 0.0005, 0.001, 0.005, 0.01, 0.02, 0.03, 0.04, 0.05, 0.06, 0.07, 0.08, 0.09, 0.1, 0.15, 0.2, 0.25, 0.3, 0.35, 0.4, 0.45, or 0.5. In some embodiments, the drug mass fractions of two or more layers of an erodible stimulant material admixed with an ADHD stimulant of a multi-layered structure are the same. In some embodiments, the drug mass fractions of two or more layers of an erodible stimulant material admixed with an ADHD stimulant of a multi-layered structure are different.

In some embodiments, the multi-layered structure comprises a top layer of a first erodible stimulant material admixed with an ADHD stimulant and another layer of a second erodible stimulant material admixed with the ADHD stimulant. In some embodiments, the multi-layered structure comprises a top layer of a first erodible stimulant material admixed with an ADHD stimulant and all other layers of a second erodible stimulant material admixed with the ADHD stimulant. In some embodiments, the first erodible stimulant material and the second erodible stimulant material are the same. In some embodiments, the first erodible stimulant material and the second erodible stimulant material are different. In some embodiments, the first erodible stimulant material and the second erodible stimulant material are different, wherein the erosion rate of the first erodible stimulant material is slower than the second erodible stimulant material.

In some embodiments, the oral dosage form comprises a first multi-layered structure comprising an erodible non-stimulant material admixed with an ADHD non-stimulant and a second multi-layered structure comprising an erodible stimulant material admixed with an ADHD stimulant. In some embodiments, the first multi-layered structure and the second multi-layered structure have the same number of layers. In some embodiments, the first multi-layered structure and the second multi-layered structure have the same number of layers, wherein the corresponding layers of each multi-layered structure have the same layer surface area and thickness. In some embodiments, the first multi-layered structure and the second multi-layered structure have the same number of layers, wherein the corresponding layers of each multi-layered structure have a different layer surface area and/or layer thickness. In some embodiments, the first multi-layered structure and the second multi-layered structure have a different number of layers.

One of ordinary skill in the art will readily appreciate that the teachings of the present disclosure regarding separate multi-layered structures, namely a multi-layered structure comprising an erodible non-stimulant material admixed with an ADHD non-stimulant and a multi-layered structure comprising an erodible stimulant material admixed with an ADHD stimulant, may be combined to form any combination of one or more multi-layered structures configured and formulated for a desired release profile of an ADHD non-stimulant and a desired release profile of an ADHD stimulant. In some embodiments, the multi-layered structure comprises an erodible non-stimulant material admixed with an ADHD non-stimulant and an erodible stimulant material admixed with an ADHD stimulant. In some embodiments, the multi-layered structure comprises a first layer of an erodible non-stimulant material admixed with an ADHD non-stimulant and a second layer of an erodible stimulant material admixed with an ADHD stimulant. In some embodiments, the multi-layered structure comprises an erodible non-stimulant/stimulant material admixed with an ADHD stimulant and an ADHD non-stimulant.

i. Immediate Release Profiles

The oral drug dosage forms described herein provide release of an ADHD stimulant according to an immediate release profile.

In some embodiments, the immediate release profile is release of substantially all of an ADHD stimulant of an oral drug dosage form within about 60 minutes of administration, such as within about any of 55 minutes, 50 minutes, 45 minutes, 40 minutes, 35 minutes, 30 minutes, 25 minutes, 20 minutes, 15 minutes, 10 minutes, 9 minutes, 8 minutes, 7 minutes, 6 minutes, 5 minutes, 4 minutes, 3 minutes, 2 minutes, or 1 minute of administration.

In some embodiments, the immediate release profile is release of at least about 85% of an ADHD stimulant of an oral drug dosage form, such as release of at least about any of 87.5%, 90%, 92.5%, 95%, 97.5%, or 100%, in less than about 15 minutes, such as less than about any of 14 minutes, 13 minutes, 12 minutes, 11 minutes, 10 minutes, 9 minutes, 8 minutes, 7 minutes, 6 minutes, 5 minutes, 4 minutes, 3 minutes, 2 minutes, or 1 minute.

In some embodiments, the immediate release profile is a burst release profile. In some embodiments, the immediate release profile is a bolus release profile.

ii. Sustained Release Profiles

The oral drug dosage forms described herein provide release of an ADHD stimulant according to a sustained release profile.

In some embodiments, the oral drug dosage forms described herein provide controlled (e.g., desired) release of an ADHD stimulant over at least about 4 hours, such as at least about any of 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, or 24 hours. In some embodiments, the oral drug dosage forms described herein provide controlled (e.g., desired) release of an ADHD stimulant over about any of 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, or 24 hours.

In some embodiments, the sustained release profile comprises a zero-order release profile, a first-order release profile, a delayed release profile, a pulsed release profile, an iterative pulsed release profile, or a combination thereof.

In some embodiments, the sustained release profile is similar, e.g., equivalent or bioequivalent, to a desired drug release profile or a release profile of a reference oral drug dosage form. In some embodiments, the desired drug release profile, e.g., sustained release profile, of an oral drug dosage form is similar, e.g., equivalent or bioequivalent, to the in vitro dissolution rate of the oral drug dosage form. In some embodiments, the desired drug release profile of an oral drug dosage form is similar, e.g., equivalent or bioequivalent, to the in vivo drug release profile of the oral drug dosage form. In some embodiments, the in vivo drug release profile of an oral drug dosage form is based on evaluation of the in vitro dissolution rate of the oral drug dosage form. In some embodiments, the desired drug release profile of an oral drug dosage form is similar, e.g., equivalent or bioequivalent, to the release profile of a reference oral drug dosage form.

In some embodiments, the dissolution similarity is evaluated using the similarity factor. In some embodiments, the dissolution similarity is evaluated using Chow's method.

In some embodiments, the release of the ADHD stimulant is measured at one or more of about pH 2, about pH 7.0, and about pH 4.5.

iii. ADHD Stimulants

The oral drug dosage forms described herein comprise an erodible stimulant material admixed with an ADHD stimulant. ADHD stimulants act by, e.g., (i) inhibiting reuptake of norepinephrine and dopamine into presynaptic neurons (e.g., methylphenidates such as methylphenidate (d,l) and dexmethylphenidate); and (ii) promoting release of dopamine and norepinephrine from presynaptic neurons and inhibiting reuptake (e.g., amphetamines such as mixed amphetamine salts, dextroamphentamine, and lisdexamfetamine (prodrug)).

In some embodiments, the ADHD stimulant is a neuromodulator. In some embodiments, the ADHD stimulant is an agent that increases the levels of dopamine in an individual. In some embodiments, the ADHD stimulant is an agent that increases the levels of norepinephrine in an individual. In some embodiments, the ADHD stimulant is a norepinephrine-dopamine reuptake inhibitor. In some embodiments, the ADHD stimulant is a dopamine transporter inhibitor. In some embodiments, the ADHD stimulant is a norepinephrine transporter inhibitor. In some embodiments, the ADHD stimulant is a serotonin transporter inhibitor.

In some embodiments, the ADHD stimulant is an amphetamine, a methylphenidate, pharmaceutically acceptable salts thereof, or a combination thereof. In some embodiments, the ADHD stimulant is an amphetamine. In some embodiments, the ADHD stimulant is a methylphenidate.

In some embodiments, the amphetamine is amphetamine or methamphetamine. Amphetamines include, but are not limited to, levoamphetamine, levamfetamine, dextroamphetamine, dexamfetamine, lisdexamfetamine, α-methylphenethylamine, D-amphetamine, (S)-amphetamine, (+)-amphetamine, (R)-amphetamine, (−)-amphetmaine, or L-amphetmaine, and pharmaceutically acceptable salts thereof, including for example, dextroamphetamine aspartate monohydrate, dextroamphetamine sulfate, amphetamine sulfate, mixed salt amphetamines, and dextroamphetamine saccharate, or a combination thereof.

In some embodiments, the methamphetamine is methamphetamine, metamfetamine, or pharmaceutically acceptable salts thereof, including methamphetamine hydrochloride. Methylphenidates include, but are not limited to, N-methylamphetamine, N,α-dimethylphenethylamine, and desoxyephedrine.

In some embodiments, the methylphenidate is methylphenidate, dextromethylphenidate (dexmethylphenidate), methyl phenidyacetate, a pharmaceutically acceptable salt thereof, including methylphenidate HCl, dexmethylphenidate HCl, or a combination thereof.

In some embodiments, the amount of an ADHD stimulant in an oral drug dosage form is about 1 mg to about 60 mg, such as any of about 1.75 mg to about 60 mg, about 1.75 mg to about 20 mg, or about 2.5 mg to about 50 mg. In some embodiments, the amount of an ADHD stimulant in an oral drug dosage form is less than about 60 mg, such as less than about any of 55 mg, 50 mg, 45 mg, 40 mg, 35 mg, 30 mg, 25 mg, 20 mg, 15 mg, 14 mg, 13 mg, 12 mg, 11 mg, 10 mg, 9 mg, 8 mg, 7 mg, 6 mg, 5 mg, 4.5 mg, 4 mg, 3.5 mg, 3 mg, 2.5 mg, 2 mg, 1.75 mg, or 1.5 mg. In some embodiments, the amount of an ADHD stimulant in an oral drug dosage form is greater than about 1 mg, such as greater than about any of 1.5 mg, 1.75 mg, 2 mg, 2.5 mg, 3 mg, 3.5 mg, 4 mg, 4.5 mg, 5 mg, 6 mg, 7 mg, 8 mg, 9 mg, 10 mg, 11 mg, 12 mg, 13 mg, 14 mg, 15 mg, 20 mg, 25 mg, 30 mg, 35 mg, 40 mg, 45 mg, 50 mg, 55 mg, or 60 mg. In some embodiments, the amount of an ADHD stimulant in an oral drug dosage form is about any of 1 mg, 1.5 mg, 1.75 mg, 2 mg, 2.5 mg, 3 mg, 3.5 mg, 4 mg, 4.5 mg, 5 mg, 6 mg, 7 mg, 8 mg, 9 mg, 10 mg, 11 mg, 12 mg, 13 mg, 14 mg, 15 mg, 20 mg, 25 mg, 30 mg, 35 mg, 40 mg, 45 mg, 50 mg, 55 mg, or 60 mg.

In some embodiments, the amount of an ADHD stimulant in an oral drug dosage form is a sub-therapeutic dose when the ADHD stimulant is not administered in conjunction with an ADHD non-stimulant.

In some embodiments, the ADHD stimulant of an oral drug dosage form is a methylphenidate or a pharmaceutically acceptable salt thereof, wherein the amount of the methylphenidate or the pharmaceutically acceptable salt thereof in the oral drug dosage form is between about 1.75 mg to about 60 mg. In some embodiments, the ADHD stimulant of an oral drug dosage form is a methylphenidate or a pharmaceutically acceptable salt thereof, wherein the amount of the methylphenidate or the pharmaceutically acceptable salt thereof in the oral drug dosage form is about any of 1.75 mg, 2 mg, 2.5 mg, 3 mg, 3.5 mg, 4 mg, 4.5 mg, 5 mg, 10 mg, 15 mg, 20 mg, 25 mg, 30 mg, 35 mg, 40 mg, 45 mg, 50 mg, 55 mg, or 60 mg.

In some embodiments, the ADHD stimulant of an oral drug dosage form is dextromethylphenidate (dexmethylphenidate) or a pharmaceutically acceptable salt thereof, wherein the amount of dextromethylphenidate or the pharmaceutically acceptable salt thereof in the oral drug dosage form is between about 1.75 mg to about 20 mg. In some embodiments, the ADHD stimulant of an oral drug dosage form is dextromethylphenidate (dexmethylphenidate) or a pharmaceutically acceptable salt thereof, wherein the amount of the dextromethylphenidate or the pharmaceutically acceptable salt thereof in the oral drug dosage form is about any of 1.75 mg, 2 mg, 2.5 mg, 3 mg, 3.5 mg, 4 mg, 4.5 mg, 5 mg, 10 mg, 15 mg, or 20 mg.

In some embodiments, the ADHD stimulant of an oral drug dosage form is dextroamphetamine or a pharmaceutically acceptable salt thereof, wherein the amount of dextroamphetamine or the pharmaceutically acceptable salt thereof in the oral drug dosage form is between about 2.5 mg to about 50 mg. In some embodiments, the ADHD stimulant of an oral drug dosage form is dextroamphetamine or a pharmaceutically acceptable salt thereof, wherein the amount of dextroamphetamine or the pharmaceutically acceptable salt thereof in the oral drug dosage form is about any of 2.5 mg, 3 mg, 3.5 mg, 4 mg, 4.5 mg, 5 mg, 10 mg, 15 mg, 20 mg, 25 mg, 30 mg, 35 mg, 40 mg, 45 mg, or 50 mg.

Those of ordinary skill in the art will recognize that the provided list of ADHD stimulants and dosages is not limiting and recognize additional ADHD stimulant pharmaceuticals and dosages which will be useful with embodiments of the present disclosure.

D. Substrate Materials

The oral drug dosage form described herein comprise an erodible non-stimulant material admixed with an ADHD non-stimulant embedded in a substrate material.

In some embodiments, the substrate material is an insulating material that is impermeable to gastrointestinal fluid, wherein the insulating material forms a barrier between the gastrointestinal fluid and a portion of an erodible non-stimulant material admixed with an ADHD non-stimulant. In some embodiments, the substrate material is an insulating material that is impermeable to gastrointestinal fluid, wherein the insulating material forms a barrier between the gastrointestinal fluid and a portion of a multi-layered structure comprising a plurality of layers of an erodible non-stimulant material admixed with an ADHD non-stimulant.

In some embodiments, the substrate material, such as an insulating material, is an erodible material. In some embodiments, the insulating material is an erodible material. In some embodiments, the substrate material has a slower erosion rate than an erodible non-stimulant material admixed with an ADHD non-stimulant. In some embodiments, the substrate material erodes at a specified pH, such as at a pH of greater than about any of 3, 3.5, 4, 4.5, 5, 5.5, 6, 6.5, or 7.

In some embodiments, the barrier formed by a substrate material around an erodible non-stimulant material admixed with an ADHD non-stimulant has a uniform thickness. In some embodiments, the barrier formed by a substrate material around an erodible non-stimulant material admixed with an ADHD non-stimulant has a varied thickness. In some embodiments, the barrier formed by a substrate material is at least about 0.01 mm, such as at least about any of 0.05 mm, 0.1 mm, 0.15 mm, 0.2 mm, 0.25 mm, 0.3 mm, 0.35 mm, 0.4 mm, 0.45 mm, 0.5 mm, 0.55 mm, 0.6 mm, 0.65 mm, 0.7 mm, 0.75 mm, 0.8 mm, 0.85 mm, 0.9 mm, 0.95 mm, or 1 mm.

Figure 2A:
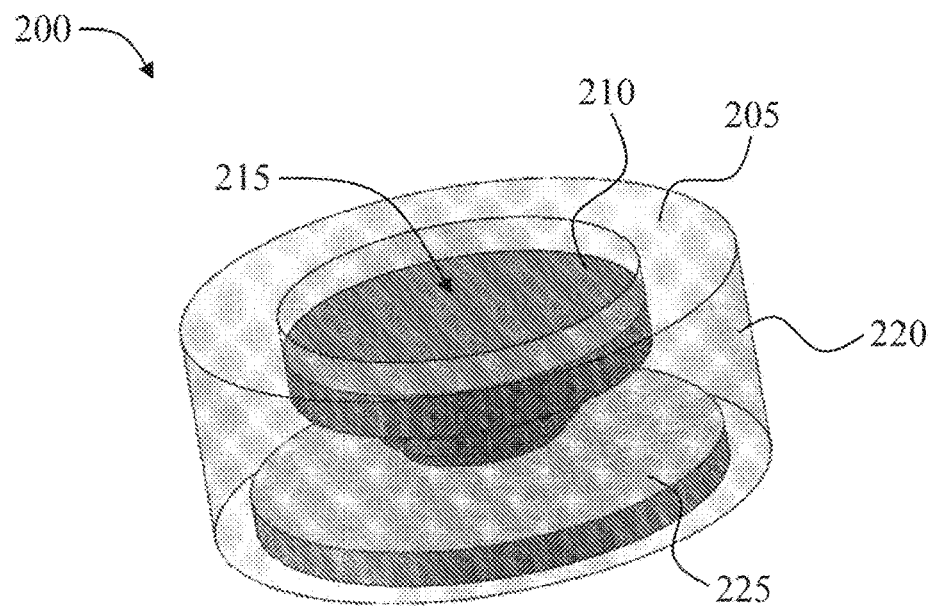
FIG. 2A and FIG. 2B show an exemplary oral drug dosage form 200.

In some embodiments, the oral drug dosage forms described herein further comprise a layer of a substrate material that forms a substrate rim, wherein the substrate rim forms a space, and wherein the space is on top of a multi-layered structure. For example, as shown in FIG. 2A, the exemplary oral drug dosage form 200 comprises a substrate material that forms a rim 205 above the top of a multi-layered structure comprising a plurality of layers of an erodible non-stimulant material admixed with an ADHD non-stimulant 210. The rim form the space 215 shown in FIG. 2A. In some embodiments, the substrate rim is at least about 0.01 mm (as measured from the top of a multi-layered structure of an erodible non-stimulant material admixed with an ADHD non-stimulant), such as at least about any of 0.05 mm, 0.1 mm, 0.15 mm, 0.2 mm, 0.25 mm, 0.3 mm, 0.35 mm, 0.4 mm, 0.45 mm, 0.5 mm, 0.55 mm, 0.6 mm, 0.65 mm, 0.7 mm, 0.75 mm, 0.8 mm, 0.85 mm, 0.9 mm, 0.95 mm, or 1 mm.

In some embodiments, the space is not filled with a material. In some embodiments, the space is filled with an erodible material. In some embodiments, the space is filled with an erodible material admixed with a drug, such as an ADHD stimulant.

E. Erodible Materials of the Oral Drug Dosage Forms

The erodible material described herein, such as an erodible non-stimulant material, an erodible stimulant material, erodible intermediate material, or a substrate material, may comprise a thermoplastic material.

In some embodiments, the thermoplastic material is edible (i.e., suitable for consumption by an individual). In some embodiments, the thermoplastic material is selected from the group consisting of a hydrophilic polymer, a hydrophobic polymer, a swellable polymer, a non-swellable polymer, a porous polymer, a non-porous polymer, an erodible polymer (such as a dissolvable polymer), a pH sensitive polymer, a natural polymer (such as shellac), a wax-like material, and a combination thereof. In some embodiments, the thermoplastic material is selected from the group consisting of polyvinyl caprolactam-polyvinyl acetate-polyethylene glycol graft copolymer 57/30/13, polyvinylpyrrolidone-co-vinyl-acetate (PVP-VA), polyvinylpyrrolidone-polyvinyl acetate copolymer (PVP-VA) 60/40, polyvinylpyrrolidone (PVP), polyvinyl acetate (PVAc) and polyvinylpyrrolidone (PVP) 80/20, vinylpyrrolidone-vinyl acetate copolymer (VA64), polyethylene glycol-polyvinyl alcohol graft copolymer 25/75, kollicoat IR-polyvinyl alcohol 60/40, polyvinyl alcohol (PVA or PV-OH), poly(vinyl acetate) (PVAc), an (optionally alkyl-, methyl-, or ethyl-) acrylate, a methacrylate copolymer, an ethacrylate copolymer, poly(butyl methacrylate-co-(2-dimethylaminoethyl) methacrylate-co-methyl methacrylate) 1:2:1, poly(dimethylaminoethylmethacrylate-co-methacrylic esters), poly(ethyl acrylate-co-methyl methacrylate-co-trimethylammonioethyl methacrylate chloride), poly(methyl acrylate-co-methyl methacrylate-co-methacrylic acid) 7:3:1, poly(methacrylic acid-co-methylmethacrylate) 1:2, poly(methacylic acid-co-ethyl acrylate) 1:1, poly(methacylic acid-co-methyl methacrylate) 1:1, poly(ethylene oxide) (PEO), poly(ethylene glycol) (PEG), hyperbranched polyesteramide, a cellulose or cellulose derivative, hydroxypropyl methylcellulose phthalate, hypromellose phthalate, hydroxypropyl methylcellulose or hypromellose (HMPC), hydroxypropyl methylcellulose acetate succinate or hypromellose acetate succinate (HPMCAS), poly(lactide-co-glycolide) (PLGA), carbomer, poly(ethylene-co-vinyl acetate), ethylene-vinyl acetate copolymer, polyethylene (PE), and polycaprolactone (PCL), hydroxyl propyl cellulose (HPC), polyoxyl 40 hydrogenerated castor oil, methyl cellulose (MC), ethyl cellulose (EC), poloxamer, hydroxypropyl methylcellulose phthalate (HPMCP), poloxamer, hydrogenated castor and soybean oil, glyceryl palmitostearate, carnauba wax, polylactic acid (PLA), polyglycolic acid (PGA), cellulose acetate butyrate (CAB), colloidal silicon dioxide, a saccharide, glucose, polyvinyl acetate phthalate (PVAP), a wax, beeswax, hydrogel, gelatin, hydrogenated vegetable oil, polyvinyl acetal diethyl aminolactate (AEA), paraffin, shellac, sodium alginate, cellulose acetate phthalate (CAP), fatty oil, arabic gum, xanthan gum, glyceryl monostearate, octadecanoic acid, and a combination thereof.

In some embodiments, the erodible material comprises a non-thermoplastic material. In some embodiments, the erodible material is a non-thermoplastic material. In some embodiments, the non-thermoplastic material is selected from the group consisting of starch, pregelatinized starch, sodium starch glycolate (CMS-Na), sucrose, dextrin, lactose, microcrystalline cellulose (MCC), mannitol, magnesium stearate (MS), powdered silica gel, sodium alginate, titanium dioxide, glycerin, syrup, lecithin, soybean oil, tea oil, ethanol, propylene glycol, glycerol, Tween, animal fats, silicone oils, cacao butter, fatty acid glycerides, vaseline, chitosan, cetyl alcohol, stearyl alcohol, and a combination thereof.

In some embodiments, the substrate material, e.g., insulating material, is selected from the group consisting of cellulose ethers, cellulose esters and acrylic resins. In some embodiments, the insulating material is selected from the group consisting of ethylcellulose, hydroxypropylmethylcellulose, hydroxypropyl cellulose, hydroxymethylcellulose, poly(meth)acrylic acid and derivatives thereof, such as the salts, amides or esters thereof are suitable for use as thermoplastic materials. In some embodiments, the insulating material is selected from the group consisting of mono- or diglycerides of C12-C30 fatty acids, C12-C30 fatty alcohols, waxes, and a combination thereof.

In some embodiments, the thermoplastic material is admixed with another agent, such as an excipient and/or a plasticizer. In some embodiments, the thermoplastic material is admixed with an excipient. In some embodiments, the excipient is selected from the group consisting of cocoa butter, polyethylene glycol (PEG), sucrose, glucose, galactose, fructose, xyloselactose, maltose, trehalose, sorbitol, mannitol, maltodextrins, raffinose, stachyose, fructo-oligosaccharides, and a combination thereof. In some embodiments, the thermoplastic material is admixed with a plasticizer. In some embodiments, the plasticizer is triethyl citrate (TEC). In some embodiments, the plasticizer is selected from the group consisting of block copolymers of polyoxyethylene-polyoxypropylene, vitamin e polyethylene glycol succinate, hydroxystearate, polyethylene glycol (such as PEG400), macrogol cetostearyl ether 12, polyoxyl 20 cetostearyl ether, polysorbate 20, polysorbate 60, polysorbate 80, acetin, acetylated triethyl citrate, tributyl citrate, tributyl o-acetylcitrate, triethyl citrate, polyoxyl 15 hydroxystearate, peg-40 hydrogenated castor oil, polyoxyl 35 castor oil, dibutyl sebacate, diethylphthalate, glycerine, methyl 4-hydroxybenzoate, glycerol, castor oil, oleic acid, tryacetin, polyalkylene glycol, and a combination thereof.

F. Abuse Deterrence

In some embodiments, the oral drug dosage forms provided herein are configured and formulated to provide an abuse-deterrent characteristic. In some embodiments, the present disclosure provides oral drug dosage forms which deter individuals from taking unadvisable, off-prescription, off-label, unadvisable administration routes (e.g., intravenously, snorting, etc.), and/or unintended dosages of the drug dosage forms described herein. In some embodiments, the material of the substrate material and/or the erodible stimulant material admixed with an ADHD stimulant is selected based on a property of the material, e.g., crushability. In some embodiments, the oral drug dosage form further comprises an agent to deter abuse of the drug dosage form. In some embodiments, the agent to deter abuse of a drug dosage form is a nasal irritant, a mucosal irritant, a polymer composition, a surfactant, or an emetic composition. Other suitable compositions are known in the art (see, e.g., Handbook of Pharmaceutical Excipients, 4th Ed. (2003), which is hereby incorporated by references in its entirety). In some embodiments, the stimulant composition comprises an abuse deterrent. In some embodiments, the oral drug dosage form further comprises an ADHD stimulant antagonist or a non-sequestered aversive excipient.

In some embodiments, the erodible material, such as an erodible non-stimulant material, an erodible stimulant material, erodible intermediate material, or a substrate material, is selected based on a property of the material that is useful for abuse deterrence. In some embodiments, the oral drug dosage form, or component thereof, is produced using a hot melt extrusion technique. In some embodiments, the oral drug dosage form, or component thereof, is produced using a hot melt extrusion technique, wherein the hot melt extrusion technique comprises using high-molecular weight polyethylene oxide (PEO) co-melted with an ADHD stimulant.

G. Exemplary Oral Drug Dosage Forms

In some embodiments, the oral drug dosage form comprises: (a) a multi-layered structure comprising a plurality of layers of an erodible non-stimulant material admixed with an ADHD non-stimulant; and (b) an erodible stimulant material admixed with an ADHD stimulant, wherein the erodible non-stimulant material admixed with the ADHD non-stimulant is embedded in a substrate material, and wherein upon exposure to gastrointestinal fluid the ADHD non-stimulant is released according to a sustained release profile and the ADHD stimulant is released according to an immediate release profile. In some embodiments, the multi-layered structure comprises four layers of an erodible non-stimulant material admixed with and ADHD non-stimulant. In some embodiments, the sustained release profile comprises a zero-order release profile. In some embodiments, the sustained release profile is ADHD non-stimulant release over about 12 hour. In some embodiments, the ADHD non-stimulant is one or more of clonidine guanfacine, atomoxetine, or a prodrug thereof. In some embodiments, the immediate release profile is ADHD stimulant release of at least about 85% of the ADHD stimulant in the oral drug dosage form within 15 minutes after oral administration. In some embodiments, the ADHD stimulant is one or more of methylphenidate (d,l), dexmethylphenidate, mixed amphetamine salts, dextroamphetamine, lisdexamfetamine, or a prodrug thereof.

In some embodiments, the oral drug dosage form comprises: (a) a first multi-layered structure comprising a plurality of layers of an erodible non-stimulant material admixed with an ADHD non-stimulant; and (b) a second multi-layered structure comprising a plurality of layers of an erodible stimulant material admixed with an ADHD stimulant, wherein the erodible non-stimulant material admixed with the ADHD non-stimulant is embedded in a substrate material, and wherein upon exposure to gastrointestinal fluid the ADHD non-stimulant is released according to a sustained release profile. In some embodiments, the ADHD stimulant is released according to a sustained release profile.

In some embodiments, the first multi-layered structure comprises four layers of an erodible non-stimulant material admixed with and ADHD non-stimulant. In some embodiments, the sustained release profile comprises a zero-order release profile. In some embodiments, the sustained release profile is ADHD non-stimulant release over about 12 hour. In some embodiments, the ADHD non-stimulant is one or more of clonidine guanfacine, atomoxetine, or a prodrug thereof. In some embodiments, the ADHD stimulant is one or more of methylphenidate (d,l), dexmethylphenidate, mixed amphetamine salts, dextroamphetamine, lisdexamfetamine, or a prodrug thereof.

In some embodiments, the oral drug dosage form comprises: (a) a first multi-layered structure comprising a plurality of layers of an erodible non-stimulant material admixed with an ADHD non-stimulant; (b) a second multi-layered structure comprising a plurality of layers of a first erodible stimulant material admixed with an ADHD stimulant; and (c) an second erodible stimulant material admixed with the ADHD stimulant, wherein the erodible non-stimulant material admixed with the ADHD non-stimulant is embedded in a substrate material, and wherein upon exposure to gastrointestinal fluid the ADHD non-stimulant is released according to a sustained release profile, the ADHD stimulant is released from the first erodible stimulant material according to a sustained release profile, and the ADHD stimulant is released from the third erodible stimulant material according to an immediate release profile.

In some embodiments, the first multi-layered structure comprises four layers of an erodible non-stimulant material admixed with and ADHD non-stimulant. In some embodiments, the sustained release profile of the ADHD non-stimulant comprises a zero-order release profile. In some embodiments, the sustained release profile of the ADHD non-stimulant is ADHD non-stimulant release over about 12 hour. In some embodiments, the ADHD non-stimulant is one or more of clonidine guanfacine, atomoxetine, or a prodrug thereof. In some embodiments, the immediate release profile is ADHD stimulant release of at least about 85% of the ADHD stimulant in the oral drug dosage form within 15 minutes after oral administration. In some embodiments, the second erodible stimulant material admixed with the ADHD stimulant is a layer on top of the top layer of the second multi-layered structure. In some embodiments, the ADHD stimulant is one or more of methylphenidate (d,l), dexmethylphenidate, mixed amphetamine salts, dextroamphetamine, lisdexamfetamine, or a prodrug thereof.

Methods of Designing

The present disclosure provides methods of designing oral drug dosage forms comprising: (a) an erodible non-stimulant material admixed with an ADHD non-stimulant; and (b) an erodible stimulant material admixed with an ADHD stimulant, wherein the erodible non-stimulant material admixed with the ADHD non-stimulant is embedded in a substrate material, and wherein upon exposure to gastrointestinal fluid the ADHD non-stimulant is released according to a sustained release profile and the ADHD stimulant is released according to an immediate release profile.

In some embodiments, the method of designing an oral drug dosage form to provide a sustained release profile of an ADHD non-stimulant and an immediate release profile of an ADHD stimulant comprises: (a) obtaining the sustained release profile of the ADHD non-stimulant; (b) selecting an erodible non-stimulant medium; (c) obtaining an erosion rate of the non-stimulant medium; and (d) determining the thickness, surface area, and/or ADHD non-stimulant drug mass fraction correlating with the sustained release profile.

In some embodiments, the method of designing an oral drug dosage form to provide a sustained release profile of an ADHD non-stimulant and an immediate release profile of an ADHD stimulant further comprises: (e) selecting an erodible stimulant medium; (f) obtaining the total weight of the stimulant medium admixed with the ADHD stimulant; (g) obtaining the density of the stimulant medium admixed with the ADHD stimulant; and (h) obtaining the volume of the stimulant medium admixed with the ADHD stimulant; and (i) determining a shape, with the volume from step (h), of the stimulant medium admixed with the ADHD stimulant. In some embodiments, the method of designing an oral drug dosage form described herein comprises selecting a substrate material. In some embodiments, the method of designing an oral drug dosage form described herein comprises selecting a thickness of a substrate rim.

In some embodiments, the methods of designing an oral drug dosage form described herein may be performed, in whole or in part, on a computer system. In some embodiments, the computer system comprises a user interface. In some embodiments, the method comprises inputting one or more parameters of the oral drug dosage form into the computer system. In some embodiments, the computer system is used to calculate the parameters of the oral drug dosage form to provide a desired drug release profile. In some embodiments, the computer system comprises three-dimensional drawing software. In some embodiments, the computer system is used to create a three-dimensional drawing of an oral drug dosage form based on the pre-determined parameters of the oral drug dosage form. In some embodiments, the computer system comprises slicing software. In some embodiments, the computer system is used to convert a three-dimensional drawing of an oral drug dosage form into three-dimensional printing code, e.g., G code. In some embodiments, the computer system executes the three-dimensional printing code, thereby printing an oral drug dosage form.

In some embodiments, the method of designing an oral drug dosage form described herein comprises adjusting the pre-determine parameters of a layer comprising an erodible material admixed with a drug, e.g., an erodible non-stimulant material admixed with an AMID non-stimulant, the parameters including surface area, thickness, drug mass fraction, to create new parameters for the layer, wherein an equal amount of the drug is released from the prior layer parameters and the adjusted layer parameters over the erosion time of the layers. In some embodiments, the layer is a layer of a multi-layered structure of an oral drug dosage form described herein. In some embodiments, the layer is the top layer of a multi-layered structure of an oral drug dosage form described herein.

In some embodiments, the volume of the layer is adjusted. In some embodiments, the volume of the layer is increased. In some embodiments, the top layer of a multi-layered structure is increased in volume. In some embodiments, the relative amount of a drug, e.g., per amount of material in the adjusted layer is less than in the layer prior to adjustment. In some embodiments, the original layer parameters are adjusted to increase the thickness of the original layer, wherein the relative amount of the drug in the layer (e.g., the layer includes the erodible non-stimulant material and the substrate material) after adjustment is decreased as compared to the layer prior to adjustment. In some embodiments, the original layer parameters are adjusted to increase the volume of the substrate material of the layer.

In some embodiments, the layer comprising an erodible material admixed with a drug is adjusted by adding one or more intermediate layers comprising an erodible intermediate material not admixed with the drug. In some embodiments, the intermediate layer comprising an erodible intermediate material not admixed with the drug is added above the top layer comprising an erodible non-stimulant material admixed with an ADHD non-stimulant of a multi-layered structure. In some embodiments, the intermediate layer comprising an erodible intermediate material not admixed with the drug is directly below the top layer comprising an erodible non-stimulant material admixed with an ADHD non-stimulant of a multi-layered structure.

In some embodiments, the layer comprising an erodible material admixed with a drug is adjusted by selecting a substitute erodible material, wherein the parameters of the layer are adjusted according to the erosion rate of the substitute erodible material. In some embodiments, the substitute erodible material admixed with an ADHD non-stimulant has a slower erosion rate than the erodible non-stimulant material admixed with an ADHD non-stimulant. In some embodiments, the substitute erodible material admixed with an ADHD non-stimulant has a faster erosion rate than the erodible non-stimulant material admixed with an ADHD non-stimulant. In some embodiments, the top layer comprising an erodible non-stimulant material admixed with an ADHD non-stimulant of a multi-layered structure is adjusted by selecting a substitute erodible material to admixed with the ADHD non-stimulant. In some embodiments, the top layer comprising an erodible non-stimulant material admixed with an ADHD non-stimulant of a multi-layered structure is adjusted by selecting a substitute erodible material to admixed with the ADHD non-stimulant, wherein the substitute erodible material has a slower erosion rate than the erodible non-stimulant material. In some embodiments, the top layer comprising an erodible non-stimulant material admixed with an ADHD non-stimulant of a multi-layered structure is adjusted by selecting a substitute erodible material to admixed with an ADHD non-stimulant, wherein the substitute erodible material admixed with the ADHD non-stimulant has a faster erosion rate than the erodible non-stimulant material admixed with the ADHD non-stimulant.

It will be understood by those skilled in the art that the methods provided herein also encompass methods of printing and designing based on one or more of the adjusted parameters discussed herein.

Methods of Three-Dimensional Printing an Oral Drug Dosage Form

The present disclosure provides methods of three-dimensional printing an oral drug dosage form described herein. In some embodiments, the method of three-dimensional printing an oral drug dosage form formulated and configured to provide a sustained release profile of an ADHD non-stimulant and an immediate release profile of an ADHD stimulant comprises: (a) dispensing an erodible non-stimulant material admixed with an ADHD non-stimulant; (b) dispensing an erodible stimulant material admixed with an ADHD stimulant; and (c) dispensing a substrate material, wherein the erodible non-stimulant material admixed with the ADHD non-stimulant correlates with the sustained release profile and the erodible stimulant material admixed with the ADHD stimulant correlates with the immediate release profile. In some embodiments, the erodible non-stimulant material admixed with the ADHD non-stimulant forms a multi-layered structure comprising a plurality of layers of the erodible non-stimulant material admixed with the ADHD non-stimulant. In some embodiments, the multi-layered structure is dispensed according to pre-determined surface areas, thicknesses, and/or drug mass fractions of each layer of the multi-layered structure.

As used herein, "printing," "three-dimensional printing," "3D printing," "additive manufacturing," or equivalents thereof, refers to a process that produces three-dimensional objects, such as drug dosage forms, layer-by-layer using digital designs. The basic process of three-dimensional printing has been described in U.S. Pat. Nos. 5,204,055; 5,260,009; 5,340,656; 5,387,380; 5,503,785; and 5,633,021. Additional U.S. patents and patent applications that related to three-dimensional printing include: U.S. Pat. Nos. 5,490,962; 5,518,690; 5,869,170; 6,530,958; 6,280,771; 6,514,518; 6,471,992; 8,828,411; U.S. Publication Nos. 2002/0015728; 2002/0106412; 2003/0143268; 2003/0198677; 2004/0005360. The content of the above U.S. patents and patent applications is hereby incorporated by reference in their entirety.

In some embodiments, an additive manufacturing technique is used to produce an oral drug dosage forms described herein. In some embodiments, a layer-by-layer technique is used to produce an oral drug dosage forms described herein.

Different 3D printing methods have been developed for drug dosage form manufacturing in terms of raw materials, equipment, and solidification. These 3D printing methods include binder deposition (see Gibson et al., Additive Manufacturing Technologies: 3D Printing, Rapid Prototyping, and Direct Digital Manufacturing., 2 ed. Springer, New York, 2015; Katstra et al., Oral dosage forms fabricated by three dimensional printing, *J Control Release*, 66, 2000; Katstra et al., Fabrication of complex oral delivery forms by three dimensional printing, Dissertation in Materials Science and Engineering, Massachusetts Institute of Technology, 2001; Lipson et al., Fabricated: The New World of 3D printing, John Wiley & Sons, Inc., 2013; Jonathan, Karim 3D printing in pharmaceutics: a new tool for designing customized drug delivery systems, *Int J Pharm*, 499, 2016), material jetting (see Jonathan, Karim, 3D printing in pharmaceutics: a new tool for designing customized drug delivery systems, *Int J Pharm*, 499, 2016), extrusion (see Gibson et al., Additive Manufacturing Technologies: 3D Printing, Rapid Prototyping, and Direct Digital Manufacturing. 2 ed. Springer, New York, 2015), and photopolymerization (see Melchels et al., A review on stereolithography and its application in biomedical engineering. Biomaterials, 31, 2010).

In some embodiments, the drug dosage forms disclosed herein are 3D printed using an extrusion method. In some embodiments, the method of 3D printing comprises using a double screw extrusion method. In an extrusion process, material is extruded from robotically-actuated printing heads through printing nozzles. Unlike binder deposition, which requires a powder bed, extrusion methods can print on any substrate. A variety of materials can be extruded for three-dimensional printing, including thermoplastic materials disclosed herein, pastes and colloidal suspensions, silicones, and other semisolids. One common type of extrusion printing is fused deposition modeling, which uses solid polymeric filaments for printing. In fused deposition modeling, a gear system drives the filament into a heated nozzle assembly for extrusion (see Gibson et al., Additive Manufacturing Technologies: 3D Printing, Rapid Prototyping, and Direct Digital Manufacturing, 2 ed. Springer, New York, 2015).

In some embodiments, the 3D printing methods disclosed herein comprise a continuous feed method.

In some embodiments, the 3D printing methods disclosed herein comprise a batch feed method.

The method instructions for 3D printing an oral drug dosage form disclosed herein may be generated a variety of ways, including direct coding, derivation from a solid CAD model, or other means specific to the 3D printing machine's computer interface and application software. These instructions may include information on the number and spatial placement of droplets, and on general 3D print parameters such as the drop spacing in each linear dimension (X, Y, Z), and volume or mass of fluid per droplet. For a given set of materials, these parameters may be adjusted in order to refine the quality of structure created. The overall resolution of the structure created is a function of the powder particle size, the fluid droplet size, the print parameters, and the material properties.

Because 3D printing may handle a range of pharmaceutical materials and control both composition and architecture locally, 3D printing is well suited to the fabrication of drug dosage forms with complex geometry and composition in accordance with the present invention.

Manufacturing the drug dosage forms using 3D printing methods also facilitates personalized medicine. Personalized medicine refers to stratification of patient populations based on biomarkers to aid therapeutic decisions and personalized dosage form design. Modifying digital designs is easier than modifying physical equipment. Also, automated, small-scale three-dimensional printing may have negligible operating cost. Hence, 3D printing can make multiple small, individualized batches economically feasible and enable personalized dosage forms designed to improve adherence.

Personalized drug dosage forms allow for tailoring the amount of drug delivered based on a patient's mass and metabolism. 3D printed dosage forms could ensure accurate dosing in growing children and permit personalized dosing of highly potent drugs. Personalized dosage forms can also combine all of patients' medications into a single daily dose, thus improve patients' adherence to medication and treatment compliance.

In some embodiments, the methods for 3D printing of an oral drug dosage form described herein further comprise dispensing an insulating material that is impermeable to gastrointestinal fluid, wherein the insulating material forms a barrier between the gastrointestinal fluid and a portion of a multi-layered structure.

In some embodiments, the methods for 3D printing of an oral drug dosage form described herein further comprise dispensing an erodible intermediate material not admixed with the drug. In some embodiments, the erodible intermediate material is the same as an erodible non-stimulant material admixed with an ADHD non-stimulant. In some embodiments, the erodible intermediate material is different than an erodible non-stimulant material admixed with an ADHD non-stimulant.

In some embodiments, the erodible non-stimulant material admixed with the ADHD non-stimulant and the erodible stimulant material admixed with the ADHD stimulant are dispensed by different printing heads.

In some embodiments, the erodible non-stimulant material admixed with the ADHD non-stimulant, the erodible stimulant material admixed with the ADHD stimulant, and the substrate material are dispensed by different printing heads.

In some embodiments, the erodible non-stimulant material admixed with the ADHD non-stimulant, the erodible stimulant material admixed with the ADHD stimulant, the substrate material, and the erodible intermediate material are dispensed by different printing heads.

In some embodiments, the 3D printing is carried out by fused deposition modeling (FDM). In some embodiments, the 3D printing is carried out by non-filament FDM. In some embodiments, the FDM is a filament FDM. In some embodiments, the 3D printing is carried out by hot melt extrusion coupled with a three-dimensional printing technique, such as FDM. In some embodiments, the 3D printing is carried out by inkjet printing. In some embodiments, the 3D printing is carried out by selective laser sintering (SLS). In some embodiments, the 3D printing is carried out by stereolithography (SLA or SL). In some embodiments, the 3D printing is carried out by PolyJet, Multi-Jet Printing System (MJP), Perfactory, Solid Object Ultraviolet-Laser Printer, Bioplotter, 3D Bioprinting, Rapid Freeze Prototyping, Fused Deposition Modelling (FDM), Benchtop System, Selective Deposition Lamination (SDL), Laminated Objet Manufacutring (LOM), Ultrasonic Consolidation, ColorJet Printing (CJP), EOSINT Systems, Laser Engineered Net Shaping (LENS) and Aerosol Jet System, Electron Beam Melting (EBM), Laser CUSING®, Selective Laser Melting (SLM), Phenix PXTM Series, Microsintering, Digital Part Materialization (DPM), or VX System.

The 3D printing methods of the present disclosure encompass printing the materials in any order that will allow for production of an oral drug dosage form disclosed herein. In some embodiments, the method for three-dimensional printing of a drug dosage form comprises dispensing a substrate material to form a structure of a specific thickness, wherein a multi-layered structure is dispensed into the structure of the substrate material. In some embodiments, the method for three-dimensional printing of an oral drug dosage form further comprises dispensing the substrate material to form a structure of a specific thickness on top of a previously dispensed structure of the substrate material.

In some embodiments, the method for three-dimensional printing of an oral drug dosage form described herein comprises designing the oral drug dosage form, in whole or in part, on a computer system. In some embodiments, the method comprises inputting parameters of the desired drug release profile and/or an oral drug dosage form into the computer system. In some embodiments, the method comprises providing one or more parameters of the oral drug dosage form, e.g., layer surface area, thickness, drug mass fraction; erosion rate. In some embodiments, the method comprises providing the desired drug release profile. In some embodiments, the methods comprise creating a virtual image of an oral drug dosage form. In some embodiments, the method comprises creating a computer model that contains the pre-determined parameters. In some embodiments, the method comprises feeding the pre-determined parameters to a three-dimensional printer and printing an oral drug dosage form according to such pre-determined parameters. In some embodiments, the method comprises creating a three-dimensional drawing of an oral drug dosage form based on the pre-determined parameters of the oral drug dosage form, wherein the three-dimensional drawing is created on a computer system. In some embodiments, the method comprises converting, such as slicing, a three-dimensional drawing of an oral drug dosage form into three-dimensional printing code, e.g., G code. In some embodiments, the method comprises using the computer system to execute three-dimensional printing code, thereby printing an oral drug dosage form described herein.

The drug dosage forms disclosed in the present application can be printed on a commercial scale. For example, in some embodiments, the methods disclosed herein may be used to 3D print about 10,000 to about 100,000 tablets of an oral drug dosage form per hour. In some embodiments, each oral drug dosage form of a commercial batch possesses or substantially complies with one or more pre-determined dosage form characteristics described herein, e.g., printing uniformity, precision of layer thickness(es), precision of layer surface area, precision of layer active agent(s) mass fraction, precision of dosage form shape, size, and weight, precision of active agent(s) amount, and precision of active agent release profile. In some embodiments, at least about 80%, such as at least about any of 85%, 90%, or 95%, of oral drug dosage forms of a commercial batch possess or substantially comply with one or more pre-determined dosage form characteristics described herein, e.g., printing uniformity, precision of layer thickness(es), precision of layer surface area, precision of layer active agent(s) mass fraction, precision of dosage form shape, size, and weight, precision of active agent(s) amount, and precision of active agent release profile.

Methods of ADHD Treatment

The oral drug dosage forms of the present disclosure are useful for treating ADHD in an individual. In some embodiments, the oral drug dosage forms formulated and configured to provide a sustained release profile of an ADHD non-stimulant and an immediate release profile of an ADHD stimulant improve patient compliance to a course of treatment for ADHD.

In some embodiments, the individual, such as a pediatric patient, presents difficulties in compliance with scheduled administration of a traditional pharmaceutical treatment. In some embodiments, the school or work day (e.g., desire not to take medicine, desire not to take medicine in front of friends or colleagues, difficulty remembering to take medicine, etc.) makes administration of a single drug dosage form in the morning the preferred method of treatment for increasing treatment compliance.

In some embodiments, traditional ADHD stimulant treatments require a large dose of an ADHD stimulant to provide patient benefit (e.g., reduced ADHD symptoms, including, but not limited to, ease of distraction, loss of attention to details, forgetfulness, loss of focus, boredom, learning disabilities, difficulty completing projects, problems with listening, daydreaming, confusion, slow movement, difficulties processing information, difficulties following instructions, fidgeting, excessive talking, restlessness, excessive motion, impatience, and outbursts) throughout the desired time course. Large doses of an ADHD stimulant used in traditional ADHD stimulant regimes result in significant side effects such as insomnia, abdominal pain, and loss of appetite that carry over into the later part of the day or subsequent days after administration where they become life disruptive for the individual and those around the individual. In some embodiments, the oral drug dosage forms of the present disclosure provide for a reduction of the dose of the administered active agents, such as an ADHD non-stimulant or ADHD stimulant. In some embodiments, the oral drug dosage forms of the present disclosure provide for extended reduction of ADHD symptoms without detrimental side effects.

In some embodiments, the present disclosure provides methods for treating ADHD in an individual in need thereof, the methods comprising administering to the individual an oral drug dosage form described herein. In some embodiments, the method for treating ADHD in an individual in need thereof comprises administering an oral drug dosage form comprising: (a) an erodible non-stimulant material admixed with an ADHD non-stimulant; and (b) an erodible stimulant material admixed with an ADHD stimulant, wherein the erodible non-stimulant material admixed with the ADHD non-stimulant is embedded in a substrate material, and wherein upon exposure to gastrointestinal fluid the ADHD non-stimulant is released according to a sustained release profile and the ADHD stimulant is released according to an immediate release profile.

In some embodiments, the method for treating ADHD in an individual in need thereof comprises administering to the individual an oral drug dosage form, wherein the oral drug dosage form comprises: (a) a multi-layered structure comprising a plurality of layers of an erodible non-stimulant material admixed with an ADHD non-stimulant; and (b) an erodible stimulant material admixed with an ADHD stimulant, wherein the erodible non-stimulant material admixed with the ADHD non-stimulant is embedded in a substrate material, and wherein upon exposure to gastrointestinal fluid the ADHD non-stimulant is released according to a sustained release profile and the ADHD stimulant is released according to an immediate release profile. In some embodiments, the multi-layered structure comprises four layers of an erodible non-stimulant material admixed with and ADHD non-stimulant. In some embodiments, the sustained release profile comprises a zero-order release profile. In some embodiments, the sustained release profile is ADHD non-stimulant release over about 12 hour. In some embodiments, the ADHD non-stimulant is one or more of clonidine guanfacine, atomoxetine, or a prodrug thereof. In some embodiments, the immediate release profile is ADHD stimulant release of at least about 85% of the ADHD stimulant in the oral drug dosage form within 15 minutes after oral administration. In some embodiments, the ADHD stimulant is one or more of methylphenidate (d,l), dexmethylphenidate, mixed amphetamine salts, dextroamphetamine, lisdexamfetamine, or a prodrug thereof.

In some embodiments, the method for treating ADHD comprises administering an oral drug dosage form described herein based on the need of the individual. In some embodiments, the oral drug dosage form is administered once daily. In some embodiments, the oral drug dosage form is administered twice daily.

In some embodiments, the individual is an infant (e.g., <2 years), child (e.g., 2-12 years), adolescent (e.g., 13-19 years), or adult. In some embodiments, the individual is less than or about 12 years old, such as about any of 10-12 years old, 8-10 years old, 6-8 years old, 4-6 years old, 2-4 years old, or less than 2 years old. In some embodiments, the individual is about 13-19 years old, such as about 13-15 years old, 15-17 years old, or about 17-19 years old. In some embodiments, the individual is older than about 18 years old, such as about any of 18 years old, 19 years old, 20 years old, 21 years old, 22 years old, 23 years old, 24 years old, 25 years old, 26 years old, 27 years old, 28 years old, 29 years old, or great than 30 years old.

In some embodiments, the method for treating ADHD in an individual further comprises determining a fixed-dose of an ADHD non-stimulant and an ADHD stimulant for use in an oral drug dosage form described herein. For example, fixed-doses for treating ADHD in an individual can be determined by altering the dosage of an active agent, such as the ADHD non-stimulant and/or the ADHD stimulant, in a drug dosage form and monitoring the response of the individual.

Those skilled in the art will recognize that several embodiments are possible within the scope and spirit of this disclosure. The disclosure will now be described in greater detail by reference to the following non-limiting examples.

The following examples further illustrate the disclosure but, of course, should not be construed as in any way limiting its scope.

EXAMPLES

Example 1

This example demonstrates an exemplary oral drug dosage form formulated and configured to provide a sustained release of an ADHD non-stimulant and immediate release of an ADHD stimulant.

Figure 3:
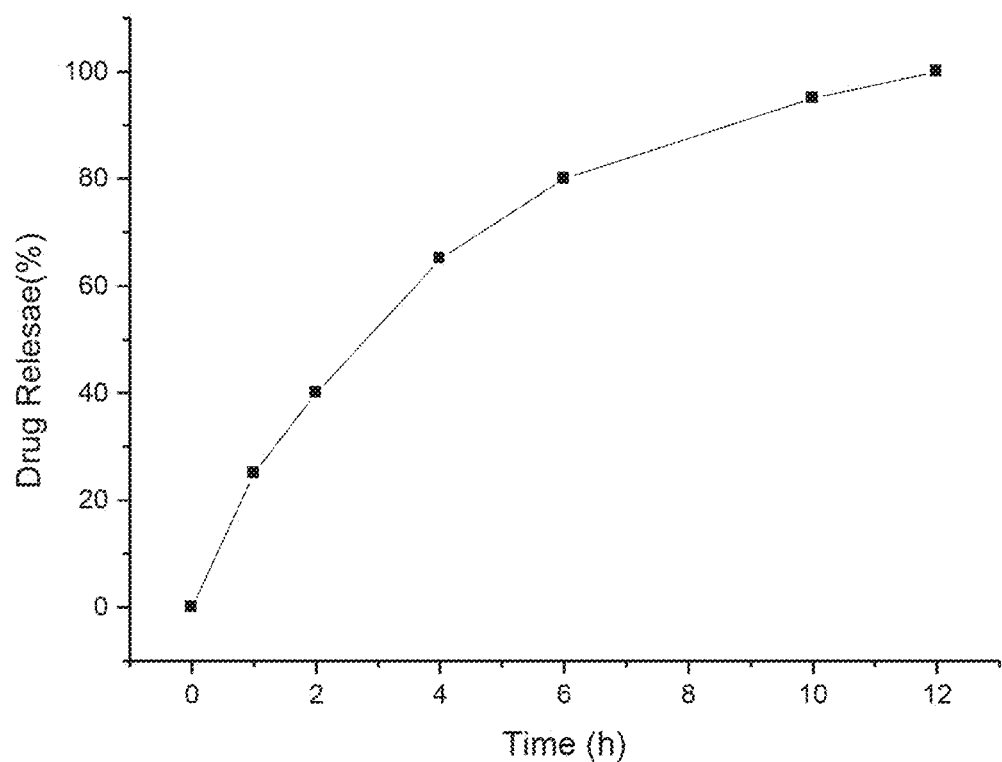
FIG. 3 shows a graph of a desired drug release profile (drug release (%) versus time (hour)).

As shown in FIG. 2A, an oral drug dosage form was designed and manufactured to provide sustained release of 0.1 mg of an ADHD non-stimulant, namely, clonidine, and immediate release of 2.5 mg of an ADHD stimulant, namely, dextromethylphenidate (dexmethylphenidate). The sustained release profile of clonidine provided by the oral drug dosage form is illustrated in FIG. 3.

The oral drug dosage form designed and manufactured comprises a multi-layered structure comprising four layers of an erodible non-stimulant material (79.68:19.92:0.4 weight ratio of hydroxyl propyl cellulose (HPC), triethyl citrate (TEC), and clonidine) (FIG. 2A, 210). The total amount of clonidine in the oral drug dosage form was 0.1 mg. The diameter and thickness of each layer (from top to bottom) of the multi-layered structure 210 was: (i) diameter 5.2 mm, thickness 0.65 mm; (ii) diameter 4.1 mm, thickness 0.26 mm; (iii) diameter 2.9 mm, thickness 0.52 mm; and (iv) diameter 2.4 mm, thickness 0.26 mm.

The erodible stimulant material admixed with an ADHD stimulant (79.2:10.8:10 weight ratio of vinylpyrrolidone-vinyl acetate copolymer (VA64), TEC, and dextromethylphenidate) was designed as a single-layered structure (FIG. 2A, 225). The total amount of dextromethylphenidate in the oral drug dosage form was 2.5 mg (propranolol HCl was used as a substitute for dextromethylphenidate as dextromethylphenidate is a controlled substance). The dimensions of the single-layered structure were: diameter 6.8 mm and thickness 0.52 mm.

The overall dimensions of the oral drug dosage form were: diameter 8.0 mm and thickness 3.12 mm. The multi-layered structure comprising clonidine and the single-layered structure comprising dextromethylphenidate was embedded in a substrate material of EUDRAGIT® RSPO (copolymer of ethyl acrylate, methyl methacrylate, and trimethylammonioethyl methacrylate chloride). The separation of the multi-layered structure comprising clonidine and the single-layered structure comprising dextromethylphenidate was 0.52 mm. The substrate material was also used to form a rim 205 that extended 0.52 mm from the top of the multi-layered structure (the space formed is indicated 215).

Figure 2B:
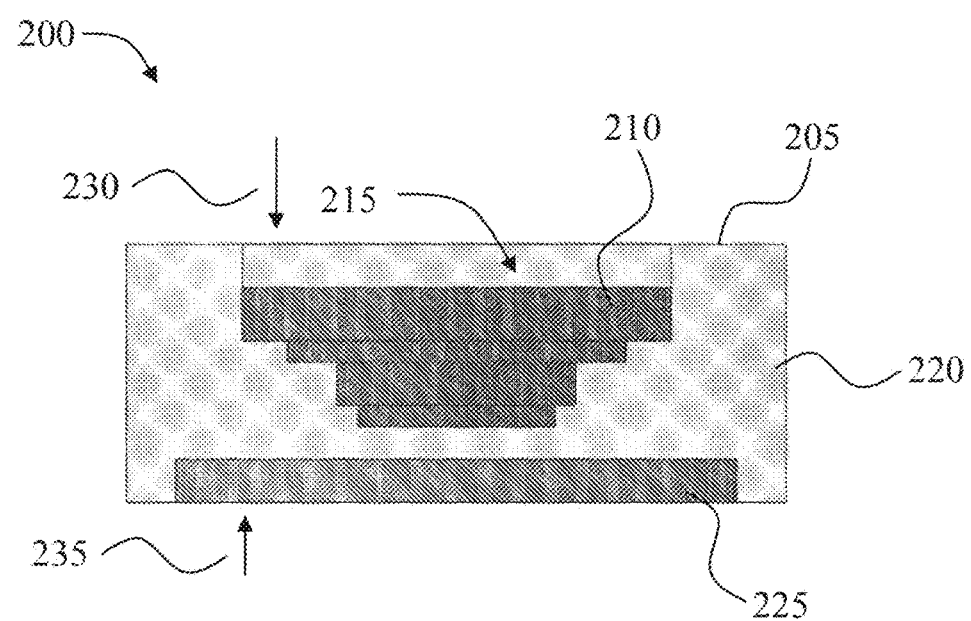

FIG. 2B provides a cross section view of the oral drug dosage form. As illustrated in FIG. 2B, the directions of erosion of the multi-layered structure comprising clonidine and the single-layered structure comprising dextromethylphenidate are indicated by respective arrows 230, 235.

The oral drug dosage form was manufactured, namely, produced using a three-dimensional printing technique, using the settings provided in Table 1.

TABLE 1

| Three-dimensional printing settings. | | |
|---|---|---|
| Erodible non-stimulant material | Machine barrel temperature | 90° C. |

TABLE 1-continued

Three-dimensional printing settings.

| | | |
|---|---|---|
| (multi-layered structure) | Connector temperature | 95° C. |
| | Printing nozzle temperature | 115° C. |
| | Pressure | 1.2 MPa |
| Substrate material | Machine barrel temperature | 110° C. |
| | Connector temperature | 120° C. |
| | Printing nozzle temperature | 135° C. |
| | Pressure | 0.4 MPa |
| Erodible stimulant material (single-layered structure) | Machine barrel temperature | 100° C. |
| | Connector temperature | 110° C. |
| | Printing nozzle temperature | 135° C. |
| | Pressure | 1.7 MPa |

Example 2

Clinical Pilot Study of Drug Dosage Forms for the Treatment of ADHD

A multi-arm clinical study is designed to assess the efficacy of exemplary drug dosage forms for the treatment of ADHD. Six primary arms will assess drug dosage forms comprising an ADHD non-stimulant and an ADHD stimulant. Specifically, the six primary arms are as follows (1) atomoxetine HCl and dextroamphetamine sulfate; (2) atomoxetine HCl and dextromethylphenidate HCl; (3) guanfacine HCl and dextroamphetamine sulfate; (4) guanfacine HCl and dextromethylphenidate HCl; (5) clonidine HCl and dextroamphetamine sulfate; and (6) clonidine HCl and dextromethylphenidate HCl.

Each primary arm will further assess various dosage combinations of the ADHD non-stimulant and the ADHD stimulant. Specifically the following dosages for each active pharmaceutical ingredient will be assessed: (a) atomoxetine HCl (10, 18, 25, 40, 60, 80, and 100 mg); (b) guanfacine HCl (1, 2, 3, and 4 mg); (c) clonidine HCl (0.1 and 0.2 mg); (d) dextroamphetamine sulfate (5 and 10 mg); and (e) dextromethylphenidate HCl (2.5, 5, and 10 mg).

A primary goal of the study is to assess technical feasibility of the drug dosage forms, including interactions, stability, cost of goods, and release profiles. A primary goal of the study is to assess efficacy of the drug dosage forms, including combinations of an ADHD non-stimulant and an ADHD stimulant, and dosages thereof.

Correlative research is performed to determine association of the combination of an ADHD non-stimulant and an ADHD stimulant and their respective dosage with improvement of ADHD symptoms. Categories of ADHD symptoms that will be monitored include, for example, inattention, hyperactivity, and impulsivity.

Each individual must have confirmed ADHD.

What is claimed is:

1. An oral drug dosage form comprising:
   (a) an erodible non-stimulant material admixed with an attention-deficit hyperactivity disorder (ADHD) non-stimulant,
      wherein the oral drug dosage form comprises a multi-layered structure comprising a plurality of layers of the erodible non-stimulant material admixed with the ADHD non-stimulant,
      wherein each layer of the erodible non-stimulant material admixed with the ADHD non-stimulant of the multi-layered structure has a pre-determined surface area, thickness, and ADHD non-stimulant mass fraction correlating with the sustained release profile, and
      wherein the surface area of each layer of the erodible non-stimulant material admixed with the ADHD non-stimulant of the multi-layered structure is between about 4.5 mm$^2$ to about 100 mm$^2$; and
   (b) an erodible stimulant material admixed with an ADHD stimulant,
      wherein the erodible non-stimulant material admixed with the ADHD non-stimulant is embedded in a substrate material, and
      wherein upon exposure to gastrointestinal fluid the ADHD non-stimulant is released according to a sustained release profile and the ADHD stimulant is released according to an immediate release profile.

2. The oral drug dosage form of claim 1, wherein each successive layer of the erodible non-stimulant material admixed with the ADHD non-stimulant of the multi-layered structure, proceeding from the top layer to the bottom layer, has a smaller surface area.

3. The oral drug dosage form of claim 1, wherein the sustained release profile is controlled, sustained ADHD non-stimulant release over at least about 12 hours.

4. The oral drug dosage form of claim 1, wherein the immediate release profile is total ADHD stimulant release within about 30 minutes.

5. The oral drug dosage form of claim 1, wherein the amount of the ADHD non-stimulant in the oral drug dosage form is a sub-therapeutic dose when the ADHD non-stimulant is administered without the ADHD stimulant.

6. The oral drug dosage form of claim 1, wherein the ADHD non-stimulant is selected from the group consisting of clonidine or a pharmaceutically acceptable salt thereof, atomoxetine or a pharmaceutically acceptable salt thereof, and guanfacine or a pharmaceutically acceptable salt thereof.

7. The oral drug dosage form of claim 6, wherein the ADHD non-stimulant is clonidine or the pharmaceutically acceptable salt thereof and the amount of clonidine or the pharmaceutically acceptable salt thereof in the oral drug dosage form is between about 0.05 mg to about 0.3 mg.

8. The oral drug dosage form of claim 6, wherein the ADHD non-stimulant is atomoxetine or the pharmaceutically acceptable salt thereof and the amount of atomoxetine or the pharmaceutically acceptable salt thereof in the oral drug dosage form is between about 2.5 mg to about 100 mg.

9. The oral drug dosage form of claim 6, wherein the ADHD non-stimulant is guanfacine or the pharmaceutically acceptable salt thereof and the amount of guanfacine or the pharmaceutically acceptable salt thereof in the oral drug dosage form is between about 0.5 mg to about 4 mg.

10. The oral drug dosage form of claim 1, wherein the ADHD stimulant is selected from the group consisting of a methylphenidate or the pharmaceutically acceptable salt thereof, dextromethylphenidate or a pharmaceutically acceptable salt thereof, an amphetamine or a pharmaceutically acceptable salt thereof, and dextroamphetamine or a pharmaceutically acceptable salt thereof.

11. The oral drug dosage form of claim 10, wherein the ADHD stimulant is the methylphenidate or the pharmaceutically acceptable salt thereof and the amount of the methylphenidate or the pharmaceutically acceptable salt thereof in the oral drug dosage form is between about 1.75 mg to about 60 mg.

12. The oral drug dosage form of claim 10, wherein the ADHD stimulant is dextromethylphenidate or the pharmaceutically acceptable salt thereof and the amount of dextromethylphenidate or the pharmaceutically acceptable salt thereof in the oral drug dosage form is between about 1.75 mg to about 20 mg.

13. The oral drug dosage form of claim 10, wherein the ADHD stimulant is dextroamphetamine or the pharmaceutically acceptable salt thereof and the amount of dextroamphetamine or the pharmaceutically acceptable salt thereof in the oral drug dosage form is between about 2.5 mg to about 50 mg.

14. A method for treating ADHD in an individual in need thereof, the method comprising administering to the individual an oral drug dosage form of claim 1.

15. The oral drug dosage form of claim 1, wherein each successive layer of the erodible non-stimulant material admixed with the ADHD non-stimulant of the multi-layered structure, proceeding from the top layer to the bottom layer, has the same surface area.

16. An oral drug dosage form comprising:
(a) a multi-layered structure comprising a plurality of layers an erodible non-stimulant material admixed with an attention-deficit hyperactivity disorder (ADHD) non-stimulant,
wherein the erodible non-stimulant material comprises hydroxyl propyl cellulose admixed with triethyl citrate, and
wherein the ADHD non-stimulant is clonidine; and
(b) an erodible stimulant material admixed with an ADHD stimulant,
wherein the erodible stimulant material is vinylpyrrolidone-vinyl acetate copolymer admixed with triethyl citrate, and
wherein the ADHD stimulant is dextromethylphenidate,
wherein the erodible non-stimulant material admixed with the ADHD non-stimulant is embedded in a substrate material, and
wherein upon exposure to gastrointestinal fluid the ADHD non-stimulant is released according to a sustained release profile and the ADHD stimulant is released according to an immediate release profile.

17. A method for three-dimensional printing of an oral drug dosage form formulated and configured to provide a sustained drug release profile of an attention-deficit hyperactivity disorder (ADHD) non-stimulant and an immediate drug release profile of an ADHD stimulant, wherein the oral drug dosage form comprises (i) an erodible non-stimulant material admixed with ADHD non-stimulant; and (ii) an erodible stimulant material admixed with an ADHD stimulant, wherein the erodible non-stimulant material admixed with the ADHD non-stimulant is embedded in a substrate material, wherein the substrate material is an insulating material that is impermeable to gastrointestinal fluid, wherein the insulating material forms a barrier between the gastrointestinal fluid and a portion of the erodible non-stimulant material, wherein upon exposure to gastrointestinal fluid the ADHD non-stimulant is released according to a sustained release profile and the ADHD stimulant is released according to an immediate release profile, and wherein the non-stimulant material admixed with the ADHD non-stimulant is a multi-layered structure comprising a plurality of layers of the erodible non-stimulant material admixed with the ADHD non-stimulant, the method comprising:
(a) dispensing the erodible non-stimulant material admixed with the ADHD non-stimulant based on a pre-determined thickness, surface area, and ADHD non-stimulant mass fraction;
(b) dispensing an erodible stimulant material admixed with a ADHD stimulant; and
(c) dispensing the substrate material.

18. An oral drug dosage form comprising:
(a) an erodible non-stimulant material admixed with an attention-deficit hyperactivity disorder (ADHD) non-stimulant,
wherein the oral drug dosage form comprises a multi-layered structure comprising a plurality of layers of the erodible non-stimulant material admixed with the ADHD non-stimulant,
wherein each layer of the erodible non-stimulant material admixed with the ADHD non-stimulant of the multi-layered structure has a pre-determined surface area, thickness, and ADHD non-stimulant mass fraction correlating with the sustained release profile, and
wherein the thickness of each layer of the erodible non-stimulant material admixed with the ADHD non-stimulant of the multi-layered structure is between about 0.2 mm to about 1 mm; and
(b) an erodible stimulant material admixed with an ADHD stimulant,
wherein the erodible non-stimulant material admixed with the ADHD non-stimulant is embedded in a substrate material, and
wherein upon exposure to gastrointestinal fluid the ADHD non-stimulant is released according to a sustained release profile and the ADHD stimulant is released according to an immediate release profile.

19. The oral drug dosage form of claim 18, wherein the ADHD non-stimulant is selected from the group consisting of clonidine or a pharmaceutically acceptable salt thereof, atomoxetine or a pharmaceutically acceptable salt thereof, and guanfacine or a pharmaceutically acceptable salt thereof, and wherein the ADHD stimulant is selected from the group consisting of a methylphenidate or the pharmaceutically acceptable salt thereof, dextromethylphenidate or a pharmaceutically acceptable salt thereof, an amphetamine or a pharmaceutically acceptable salt thereof, and dextroamphetamine or a pharmaceutically acceptable salt thereof.

20. An oral drug dosage form comprising:
(a) an erodible non-stimulant material admixed with an attention-deficit hyperactivity disorder (ADHD) non-stimulant; and
(b) an erodible stimulant material admixed with an ADHD stimulant,
wherein the erodible non-stimulant material admixed with the ADHD non-stimulant is embedded in a substrate material,
wherein the substrate material is an insulating material that is impermeable to gastrointestinal fluid, wherein the insulating material forms a barrier between the gastrointestinal fluid and a portion of the erodible non-stimulant material, and
wherein upon exposure to gastrointestinal fluid the ADHD non-stimulant is released according to a sustained release profile and the ADHD stimulant is released according to an immediate release profile.

21. The oral drug dosage form of claim 20, wherein the ADHD non-stimulant is selected from the group consisting of clonidine or a pharmaceutically acceptable salt thereof, atomoxetine or a pharmaceutically acceptable salt thereof, and guanfacine or a pharmaceutically acceptable salt thereof, and wherein the ADHD stimulant is selected from the group consisting of a methylphenidate or the pharmaceutically acceptable salt thereof, dextromethylphenidate or a pharmaceutically acceptable salt thereof, an amphetamine or a pharmaceutically acceptable salt thereof, and dextroamphetamine or a pharmaceutically acceptable salt thereof.

\* \* \* \* \*